(12) United States Patent
Mirza et al.

(10) Patent No.: US 9,597,043 B1
(45) Date of Patent: Mar. 21, 2017

(54) SYSTEM AND METHOD FOR SUPPORTING A PATIENT FOR IMAGERY DURING SURGERY

(71) Applicant: Dartmouth-Hitchcock Clinic, Lebanon, NH (US)

(72) Inventors: Sohail K. Mirza, Lebanon, NH (US);
Keith D. Paulsen, Lebanon, NH (US);
John C. Peiffer, Lebanon, NH (US);
Atthar Mirza, Lebanon, NH (US)

(73) Assignee: Dartmouth-Hitchcock Clinic, Lebanon, NH (US)

( * ) Notice: Subject to any disclaimer, the term of this patent is extended or adjusted under 35 U.S.C. 154(b) by 0 days.

(21) Appl. No.: 13/905,340

(22) Filed: May 30, 2013

Related U.S. Application Data

(60) Provisional application No. 61/653,462, filed on May 31, 2012.

(51) Int. Cl.
| A47B 13/00 | (2006.01) |
| A61B 6/04 | (2006.01) |
| A61G 13/02 | (2006.01) |
| A61G 13/04 | (2006.01) |
| A61G 13/06 | (2006.01) |
| A61G 13/12 | (2006.01) |

(52) U.S. Cl.
CPC .......... *A61B 6/0421* (2013.01); *A61B 6/0407* (2013.01); *A61G 13/02* (2013.01); *A61G 13/04* (2013.01); *A61G 13/06* (2013.01); *A61G 13/1265* (2013.01)

(58) Field of Classification Search
CPC ........ A61G 13/02; A61G 13/04; A61G 13/06; A61G 13/1265; A61B 6/0421; A61B 6/0407

USPC .......... 5/607, 608, 610, 621, 430, 428, 427
See application file for complete search history.

(56) References Cited

U.S. PATENT DOCUMENTS

| 3,226,734 | A | * | 1/1966 | Coventon ........................ 5/607 |
| 5,156,166 | A | | 10/1992 | Sebring |
| 6,112,349 | A | * | 9/2000 | Connolly .......................... 5/607 |
| 6,282,736 | B1 | * | 9/2001 | Hand et al. ...................... 5/608 |
| 7,373,676 | B2 | * | 5/2008 | Markovic ............ A61N 5/1049 378/209 |

(Continued)

FOREIGN PATENT DOCUMENTS

| WO | 2009076483 A1 | 6/2009 |
| WO | 2009146522 A1 | 12/2009 |

*Primary Examiner* — David E Sosnowski
(74) *Attorney, Agent, or Firm* — Loginov & Associates, PLLC; William A. Loginov

(57) ABSTRACT

An system for supporting a patient during a medical procedure including a pedestal supported from a base surface; a ring structure mounted over the pedestal, the ring structure includes inner and outer ring members that are arranged for relative rotation therebetween. An elongated support platform, upon which the patient is supported, is also provided, as well as a bar member for mounting one end of the support platform to the inner ring of the ring structure while the opposite end of the support platform is free so as to be disposed in a cantilever manner from the ring structure. The roll of the support platform is controlled by rotating the inner ring relative to the outer ring, the pitch of the support platform by pivoting the bar member relative to the inner ring, and the yaw of the support platform by rotating the ring structure relative to the pedestal.

26 Claims, 26 Drawing Sheets

(56) References Cited

U.S. PATENT DOCUMENTS

| | | | |
|---|---|---|---|
| 7,472,440 B2 | 1/2009 | Bartlett et al. | |
| 7,640,607 B2* | 1/2010 | Guertin | A61B 6/032 378/209 |
| 8,378,325 B2* | 2/2013 | Fadler | A61N 5/1081 250/505.1 |
| 8,401,612 B1* | 3/2013 | Chu | A61G 7/1057 5/601 |
| 8,683,628 B2* | 4/2014 | Baumann | A61B 6/0457 297/135 |
| 8,692,181 B2* | 4/2014 | Gross | A61B 6/0407 250/221 |
| 8,692,213 B2* | 4/2014 | Abenaim | A61B 6/0407 250/453.11 |
| 2007/0124858 A1* | 6/2007 | Ahlman | A61B 6/0442 5/81.1 R |
| 2009/0282614 A1 | 11/2009 | Jackson | |
| 2010/0034435 A1* | 2/2010 | Kariv | A61B 5/0555 382/128 |
| 2010/0192300 A1 | 8/2010 | Tannoury et al. | |
| 2011/0107515 A1* | 5/2011 | Brunker | A61B 6/0442 5/601 |
| 2012/0174317 A1* | 7/2012 | Saracen | A61B 6/0457 5/601 |
| 2014/0033432 A1* | 2/2014 | Marle | A61G 7/1057 5/601 |
| 2014/0053333 A1* | 2/2014 | Krieg | A61B 6/487 5/601 |
| 2014/0098934 A1* | 4/2014 | Kondo | A61B 6/032 378/20 |
| 2014/0109316 A1* | 4/2014 | Jackson | A61G 13/0036 5/601 |
| 2015/0000038 A1* | 1/2015 | Obi | A61G 13/02 5/601 |
| 2015/0059093 A1* | 3/2015 | Candidus | A61B 5/0555 5/601 |

* cited by examiner

SYSTEM AND METHOD FOR SUPPORTING A PATIENT FOR IMAGERY DURING SURGERY

RELATED APPLICATION

This application claims the benefit of U.S. Provisional Application Ser. No. 61/653,462, filed May 31, 2012, entitled SYSTEM AND METHOD FOR SUPPORTING A PATIENT FOR IMAGERY DURING SURGERY, the entire disclosure of which is herein incorporated by reference.

FIELD OF THE INVENTION

This invention relates to support systems and methods for patients during medical imaging procedures, and more particularly to tables for use in surgical procedures which involve imaging as a part of the procedure, such as spinal surgery.

BACKGROUND OF THE INVENTION

Surgical practice now incorporates imaging techniques that may be used prior to, during or after surgery. At the present time it is typical to move the patient between different support system in order to perform either imaging techniques or surgical techniques. This makes the overall procedure unduly complex. Also, existing prior art tables are limited in their motion. Existing support tables require the table and secured patient to be moved into a fixed position piece of imaging equipment. Moreover, with existing support system there is a limit on the degree of scan or motion while positioned at the imaging station. Also, prior art medical systems make it difficult to perform both surgery and medical image scanning at a single location, or to offer multiple scanning options. This is primarily because these imaging devices are fixed and relatively large in size.

Accordingly, it is desirable to provide an improved patient support system and in particular an improved radiolucent spinal surgery table that allows for a high degree in flexibility in use before, during and after a surgical procedure is complete.

SUMMARY OF THE INVENTION

This invention overcomes disadvantages of the prior art by providing a system and method for supporting a patient during a medical procedure but also constructed and arranged so as to be compatible with such imaging techniques as MRI, CT or fluoroscopy. For this purpose, the system and method in an illustrative embodiment is in the form of a radiolucent spinal surgery table that is of cantilever construction. The support table is controllable in each of at least three degrees of freedom, including "roll," "pitch," and "yaw." In accordance with the patient centered system of an illustrative embodiment, the imaging system is constructed and arranged for linear motion in certain yaw positions of the support table, and during surgical procedures, the support table can be readily repositioned.

In accordance with an embodiment, there is provided an system for supporting a patient that is comprised of a pedestal supported from a base surface and a ring structure mounted over the pedestal. The ring structure includes inner and outer ring members that are constructed and arranged for relative rotation therebetween. An elongated support platform is provided upon which the patient is supported. A bar member is for mounting one end of the support platform to the inner ring of the ring structure while the opposite end of the support platform is free so as to be disposed in a cantilevered manner from the ring structure. The control of the platform includes respective control elements for controlling the "roll" of the support platform by rotating the inner ring relative to the outer ring, the "pitch" of the support platform by pivoting the bar member relative to the inner ring, and the "yaw" of the support platform by rotating the ring structure relative to the pedestal.

In accordance with another embodiment there is provided a system of patient diagnosis and the performance of surgical procedures comprising, in combination, a surgical table and at least one imaging station. The surgical table comprises a base pedestal, a motion structure disposed over the pedestal and a patient support platform upon which the patient is placed and cantilevered from the motion structure. The support platform is mounted from the motion structure and constructed and arranged for multiple degrees of motion relative to the base pedestal. The imaging station comprises an imaging device that moves in relationship to and over the cantilevered surgical table when the surgical table is in a first stationary position. In one patient-centered medical system of the illustrative embodiment there are at least two imaging stations each including an imaging device, the imaging stations separated from each other (typically opposed at 180 degrees) and each having a mechanism for controlling a linear motion of each imaging device so as to move in relationship to and over the cantilevered surgical table when the surgical table is in either of alternate positions.

BRIEF DESCRIPTION OF THE DRAWINGS

The invention description below refers to the accompanying drawings, of which.

DETAILED DESCRIPTION

Figure 1:
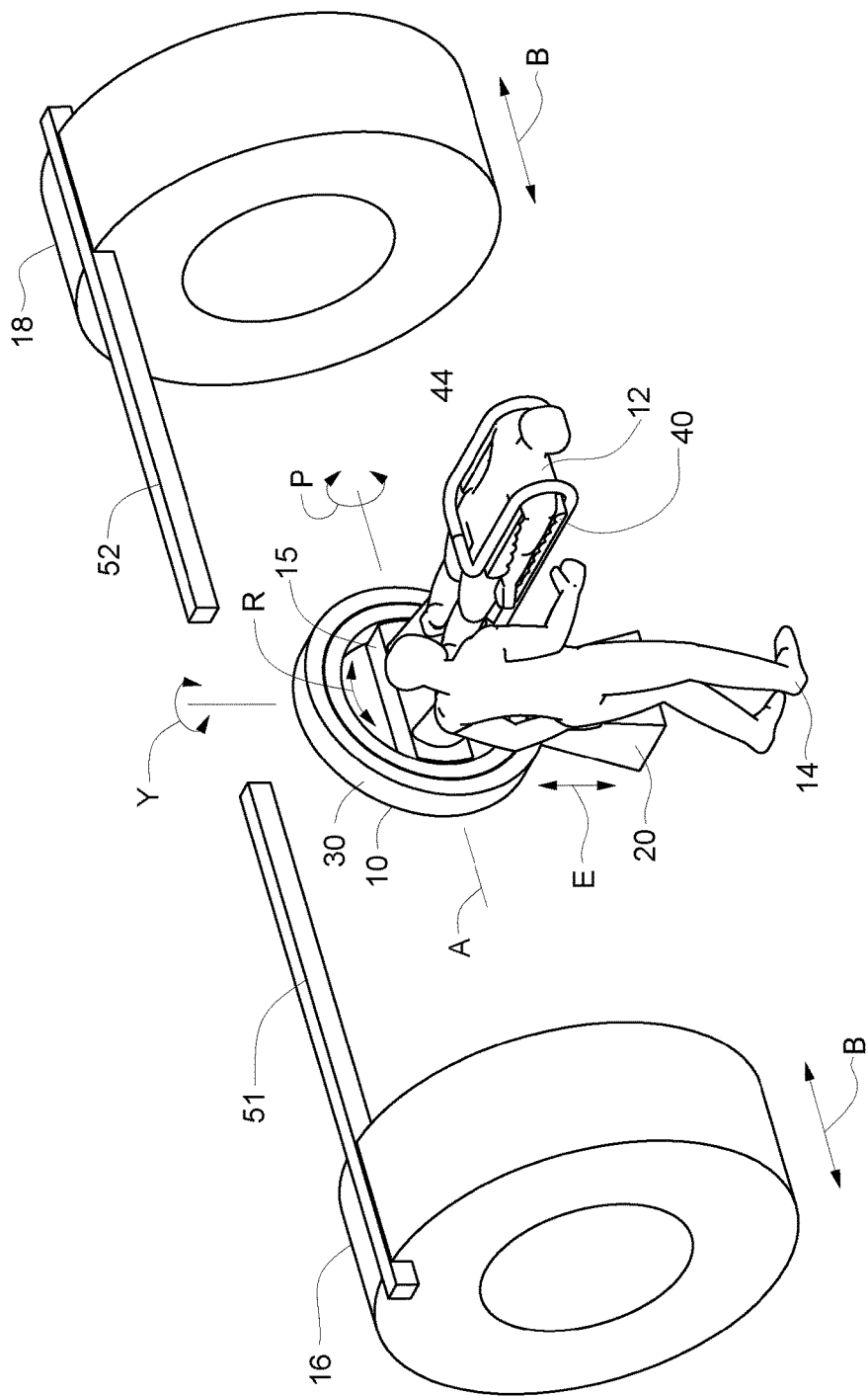
FIG. 1 is a schematic perspective view of a medical system in accordance with the present invention.

Reference is now made to the schematic perspective view of FIG. 1 for an overall illustration of a medical surgical environment employing a patient support system (also herein termed a "table") in accordance with an illustrative embodiment. In FIG. 1 the patient support system 10 is shown including a patient 12 in a supine state and an attendant 14, who can be any appropriate medical staff member. The depicted arrangement suggests that the patient is undergoing a surgical procedure involving the spine, and that area of the body is exposed to the medical staff Such procedures benefit significantly by the availability of one, and desirably several different imaging modalities. Often only one type of imaging modality can be provided in alignment with the patient or, often the patient is moved out of the operating room to a neighboring imaging center. This is inefficient, time-consuming and potentially hazardous to the patient, since any movement during surgery carries risks. Thus, in the system in accordance with the illustrative embodiment, rather than moving the patient and support table into and out of a fixed position imaging system, the imaging system itself is constructed and arranged to transition over the patient. In FIG. 1 separately disposed imaging devices 16 and 18 are schematically illustrated. The imaging system 16 can comprise a piece of MRI equipment while the imaging system 18 can comprise a piece of CT scan equipment. In FIG. 1 the imaging system is shown very schematic, but it is understood that various types of imaging devices can be used in accordance with the system of the illustrative embodiment. In this embodiment the system 16 and 18 is aligned along a longitudinal axis A. In FIG. 1 arrows B illustrate the respective direction of movement of the imaging system relative to the patient and underlying table.

FIG. 1 also depicts rails 51 and 52 which respectively guide each of the discrete imaging systems 16 and 18 toward and away from the patient 12. In FIG. 1 the position of the patient support table 10 is illustrated as substantially transverse to the axis A. This can be considered the position where surgery can be performed on the patient 12. Alternatively, the patient support table 10 can be pivoted in a "yaw" direction, substantially 90 degrees from the position illustrated in FIG. 1. This is illustrated by the curved arrow Y in FIG. 1. This pivoting or rotation can be through a total angle of at least 180 degrees, and potentially as much as 270-360 degrees. When the patient support table 10 is pivoted or rotated so that the patient is in line with axis A, then depending upon the direction of rotation, the patient is in a position for alignment with either of the imaging devices 16 or 18. Both of the imaging devices move linearly in the A axis direction upon the respective rails 51 and 52. Although the imaging stations in FIG. 1 are illustrated as disposed in opposing positions, it is understood that they can also be positioned at other angles to each other. The at least-180-degree allowance of the "yaw' motion facilitates a variety of relative angles for use in administering treatment to the patient.

It should be clear that the ability to quickly "yaw" the table so as to present the patient to each of a variety of imaging modalities is highly desirable. The imaging systems 16 and 18 advantageously pass onto the otherwise stationary patient due to their slidable suspension on overhead rails. This arrangement allows the patient to be scanned more deeply (further along his/her height than a typical stationary scanning arrangement. The structures that allow each of the scanning devices to slide along rails can be implemented in accordance with ordinary skill. In various embodiments an existing stationary scanning device can be modified in accordance with ordinary skill to allow slidable motion as shown. In alternate embodiments, one or more purpose-built slidable scanning device(s) can be employed.

Note that various directional and orientational terms as used herein, such as "up", "down", "right", "left", "front", "rear", "top", "bottom", and the like should be taken as relative conventions unless otherwise noted, and not as absolute directions with respect to a fixed coordinate system, such as the acting direction of gravity.

Figure 2:
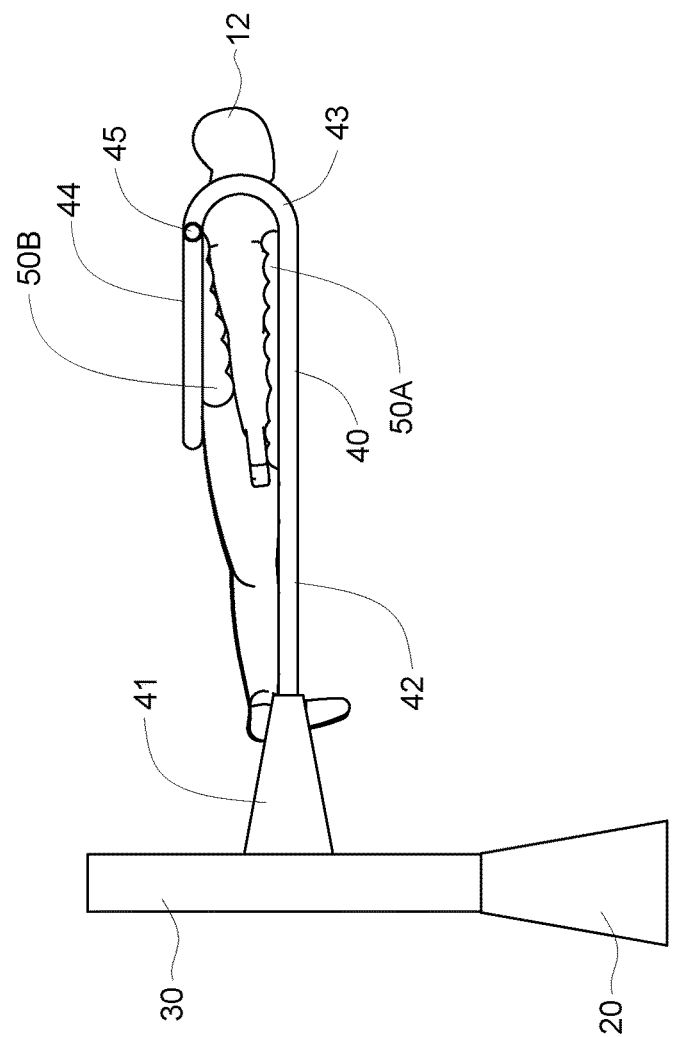
FIG. 2 is a schematic side elevation view of the support system of the present invention.

In overview, the support table 10 generally comprises a pedestal 20, a ring structure 30 and an elongated support platform 40 that is supported from the ring structure in a cantilever manner such as also illustrated in FIG. 2. The rotation or pivoting of the support platform 40 in the "yaw" direction is facilitated by either rotation of the complete pedestal and ring structure or by virtue of rotation of the ring structure 30 relative to the pedestal 20. In addition, the "roll" of the platform is performed by virtue of rotation of an inner ring of the ring structure 10 relative to an outer ring thereof. The ring structure is described in further detail hereinafter such as in FIG. 11. Refer also in FIG. 1 to the curved arrow R that illustrates the "roll" motion. In addition, the support platform 40 can be controlled as to its "pitch". This is illustrated by the curved arrow P in FIG. 1 and is accomplished by virtue of a rotation of the bar member 15 relative to an inner ring 34 of the ring structure 10. A fourth parameter is also illustrated in FIG. 1 by the arrow E which represents a change in elevation of the support system. This is advantageous in accommodating the particular height of an attendant, surgeon or other medical practitioner.

The table structure disclosed herein is constructed so as to be radiolucent along (at least) portions that are exposed to the imaging devices' field and that can potentially obscure an image of the patient's internals. In this manner the table structure can readily interface with the various imaging devices. One material for the structure can be titanium. Much of the structure, particularly the interface between the ring structure and platform, has to be constructed in a sturdy manner in order to support the cantilever action at the platform 40. Also the structure can be tubular, particularly the platform, to add strength, as well as to provide a conduit for electrical cabling or hydraulic or pneumatic tubing.

Figure 14:
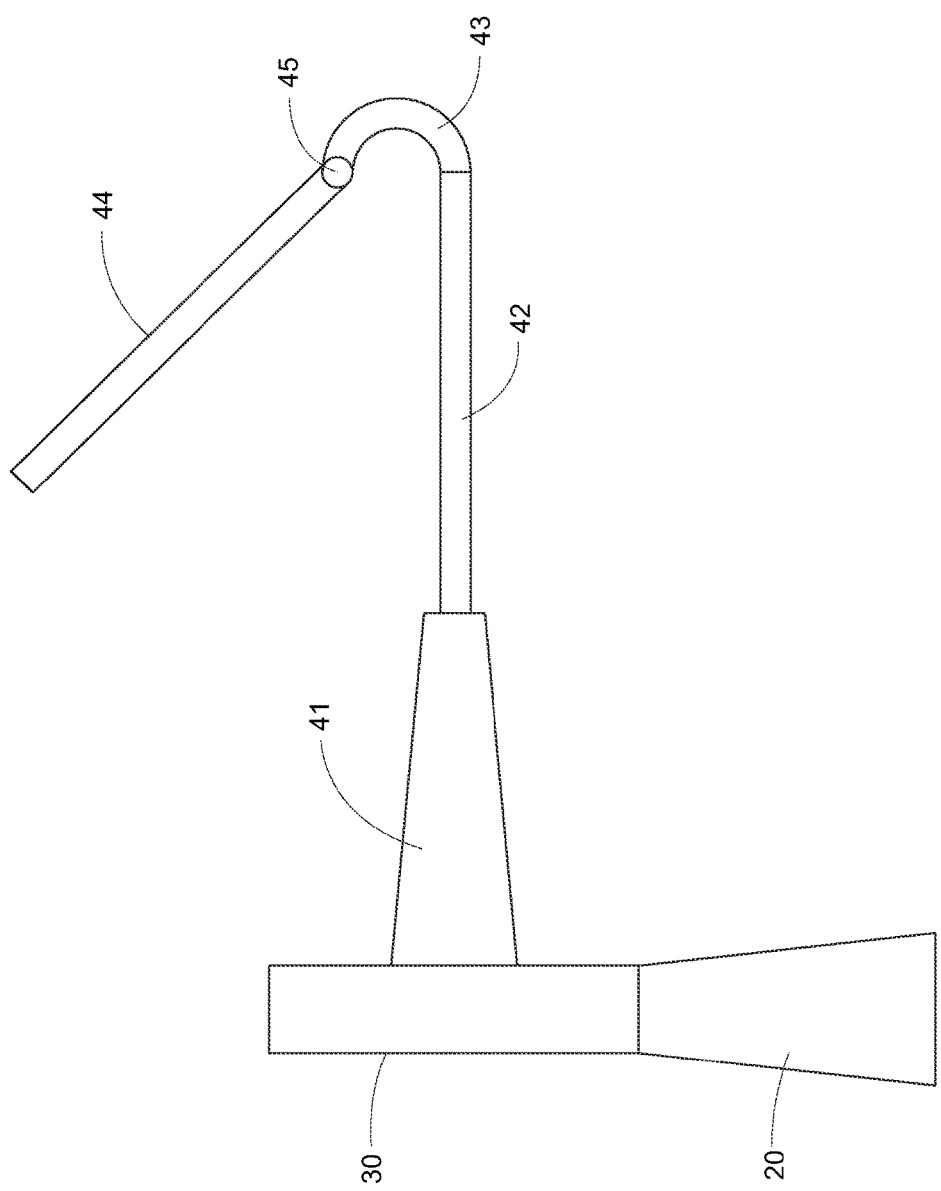
FIG. 14 is a side view of the surgery table with the restraining bar in an open position.
Figure 15:
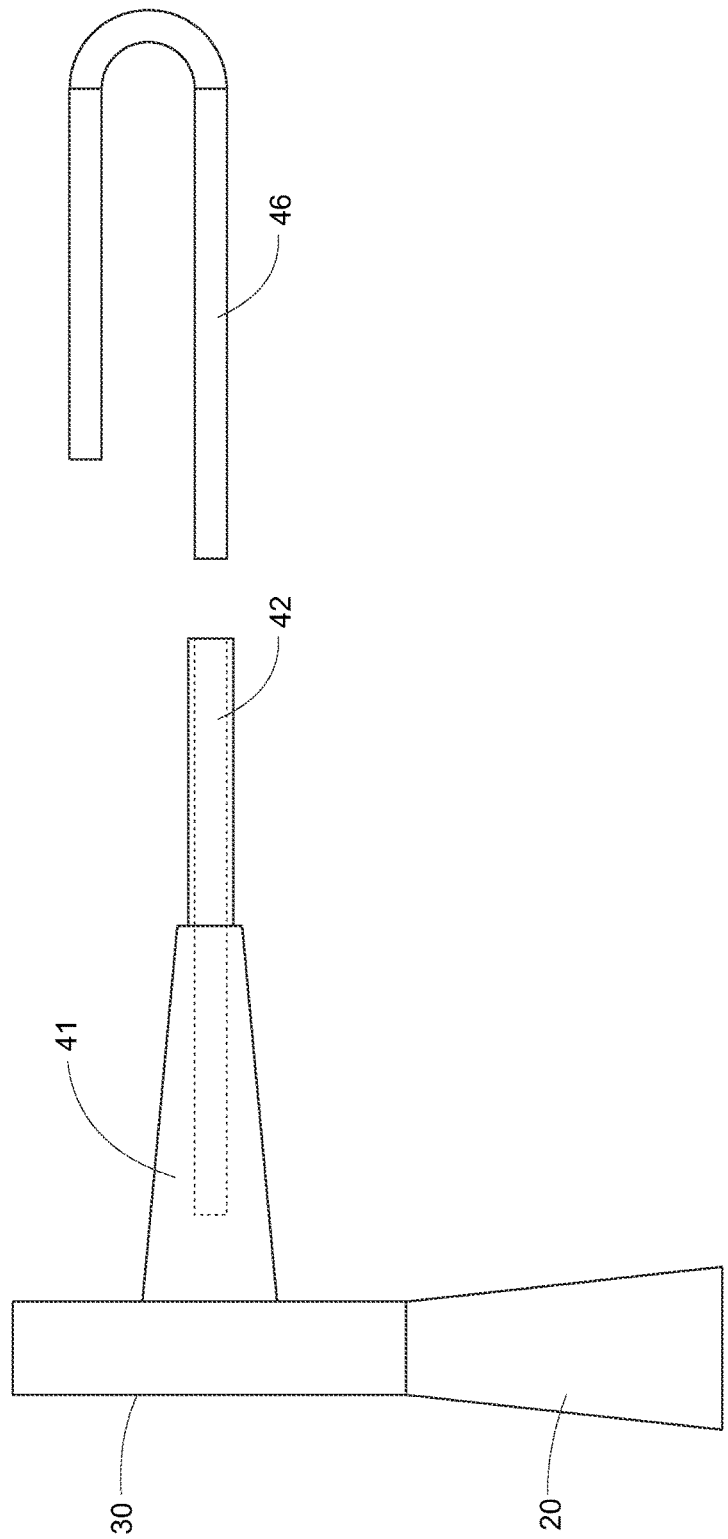
FIG. 15 is a schematic side view of an alternate embodiment of the restraining bar.

Reference is now made to FIGS. 2-6 for further details of the support table 40 which is comprised of a main pair of support legs 42 that extend from the transverse bar member 15, and a U-shaped restraining bar 44. In general, the support bar and associated table geometry are constructed and arranged to support a predetermined-size patients securely and with minimal movement during surgery and, particularly, imaging, regardless of orientation in the roll, tilt or yaw degrees (within desired limits. While not shown, supplemental, radiolucent straps can be provided at appropriate locations on the table (that permit access to surgical sites) so that the patient is ore securely restrained during the procedure. This is particularly desirable where the patient experiences roll or tilt from a non-vertical orientation and can possibly slide or shift with respect to the table. In an embodiment described herein, the pair of support legs 42 of the restraining bar are supported from the main portion of the table in a cantilever manner, and can each be provided at their base end with an enlarged (e.g. conical or otherwise tapering) base section 41, in order to provide the proper support from the bar member 15 for the cantilever arrangement illustrated. Each of the legs, as well as the restraining bar can be constructed of a tubular material that can receive control wiring, hydraulic lines or pneumatic lines, to be discussed in further detail hereinafter. In the embodiment illustrated in FIGS. 2-6, the U-shaped restraining bar 44 is pivotally attached to a turned end 43 of the pair of legs 42. This connection is at the pivot 45. In this regard refer also to the schematic side elevation view of FIG. 14 illustrating the restraining bar 44 lifted to an open position by pivoting at the pivot location 45. The restraining bar is normally in this open position in readiness for receiving and restraining a patient 12. As an alternate to the pivot arrangement illustrated in FIG. 14, reference is also made to FIG. 15 that shows one of the support legs 42 but, in place of a pivot arrangement, a sliding trombone-like restraining member 46 that can be engaged with the patient by a sliding action rather than a pivoting action. Member 46 can telescope into leg 42.

Figure 3:
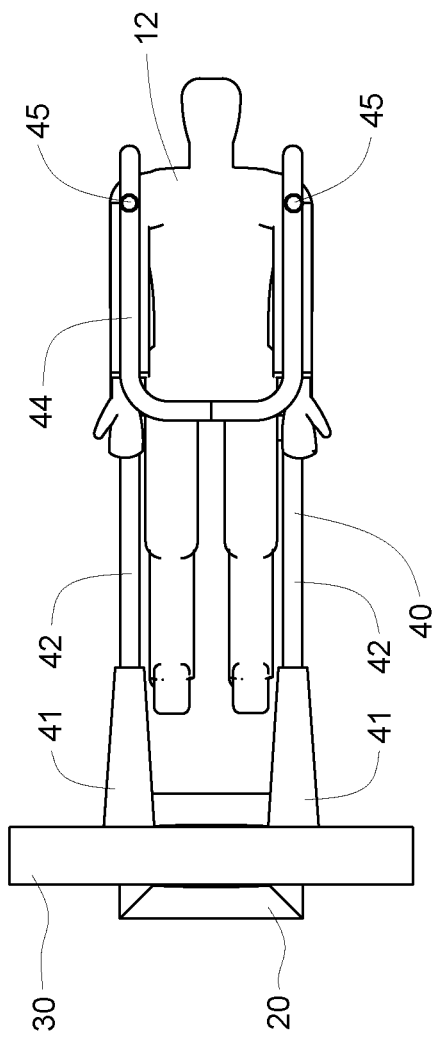
FIG. 3 is a plan view of the support system.
Figure 5:
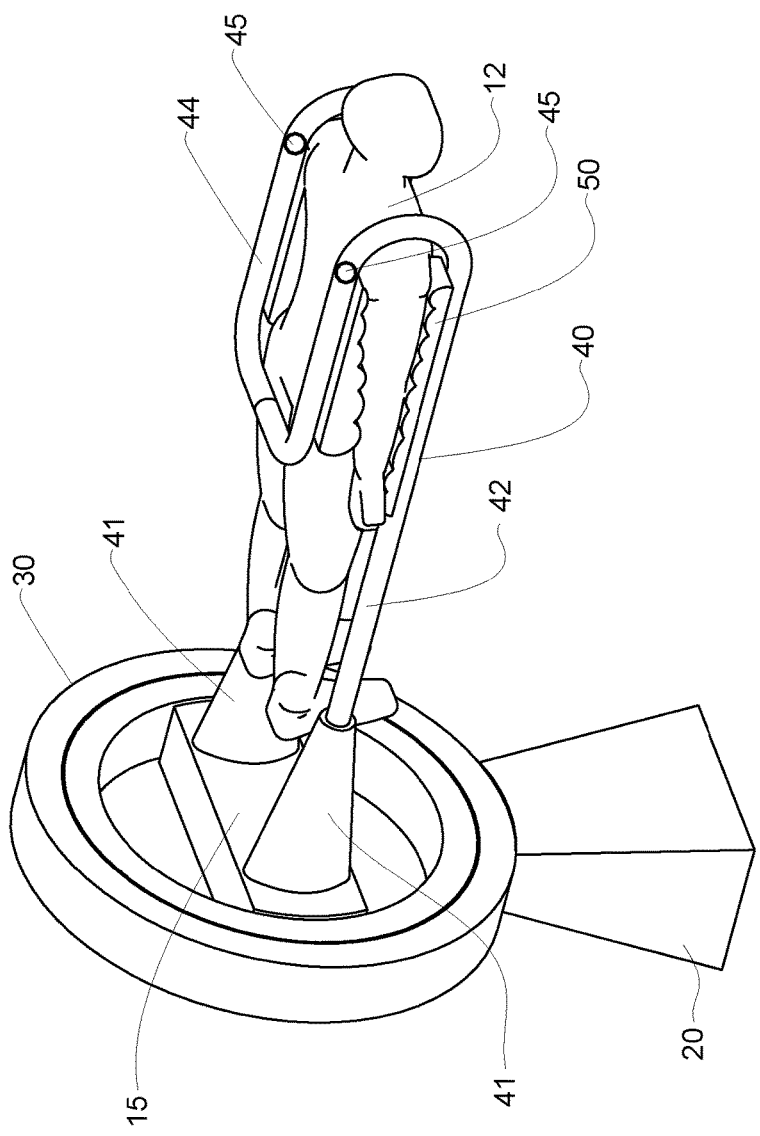
FIG. 5 is a perspective view of the support system with the system in a closed position and the support pads inflated.
Figure 6:
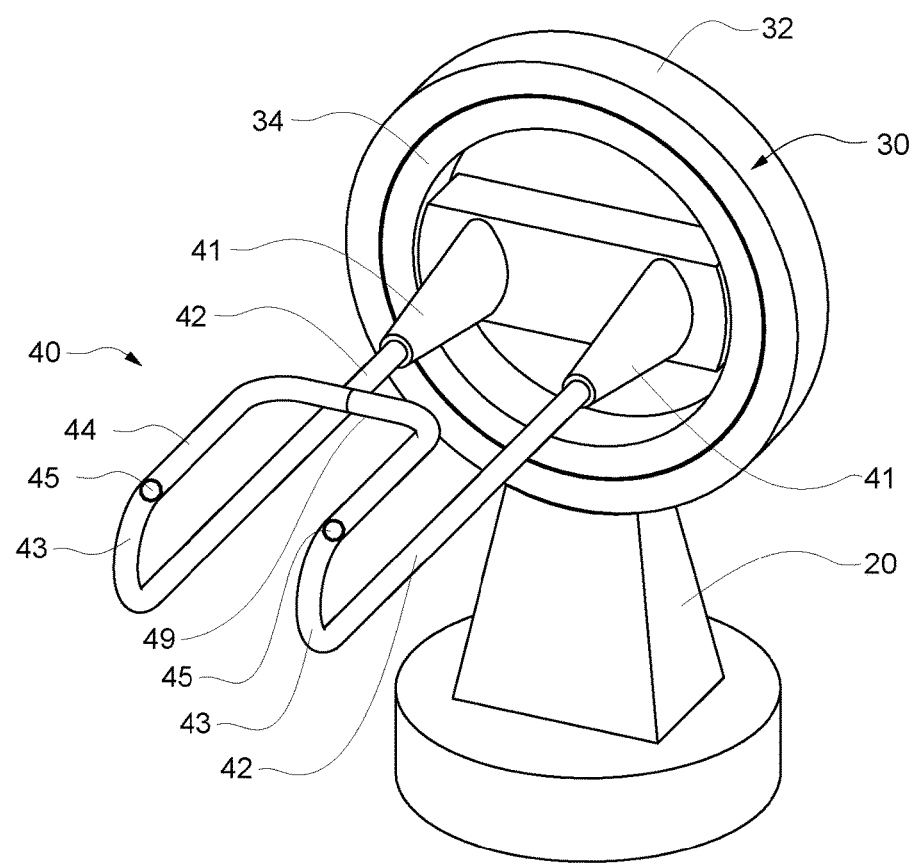
FIG. 6 is a schematic perspective view of the support system without a patient in place.
Figure 7A:
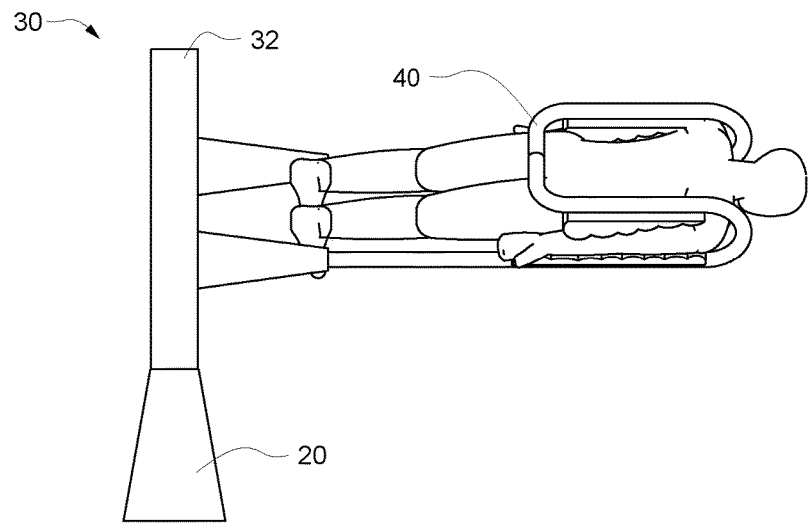
FIGS. 7A, 7B and 7c are schematic views illustrating the system's "roll" parameter. with (FIG. 7A) and without (FIGS. 7B and 7C) a patient in place.
Figure 7B:
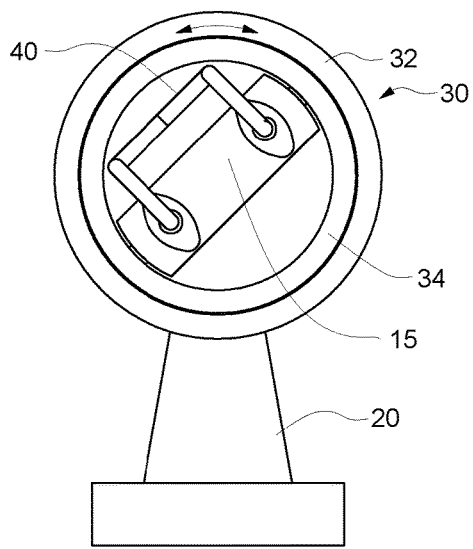
Figure 7C:
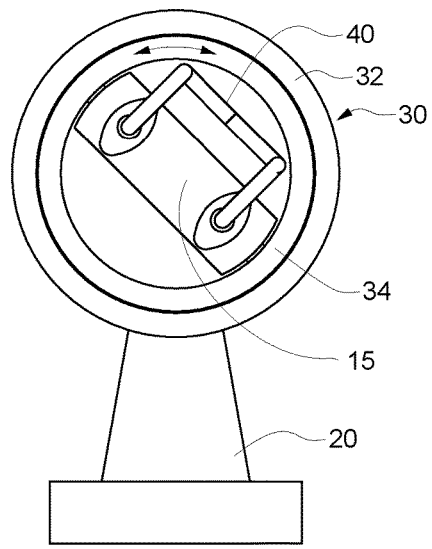

FIGS. 2, 3 and 5 illustrate the exemplary patient 12 in place on the platform 40 and held in place by the restraining bar 44. These illustrations show the patient in a prone position. However, the patient can also be initially positioned in a supine position. For spinal surgery, or for other applications, the support system of the illustrative embodiment has the capability of a partial, or full (360 degree) "roll" and thus, regardless of the initial position, the patient can be moved to any position convenient for the particular surgical procedure being performed, or for a variety of imaging poses. FIG. 6 is a schematic illustration of the platform illustrating primarily only the support legs and restraining bar, and without any patient in position.

Figure 4:
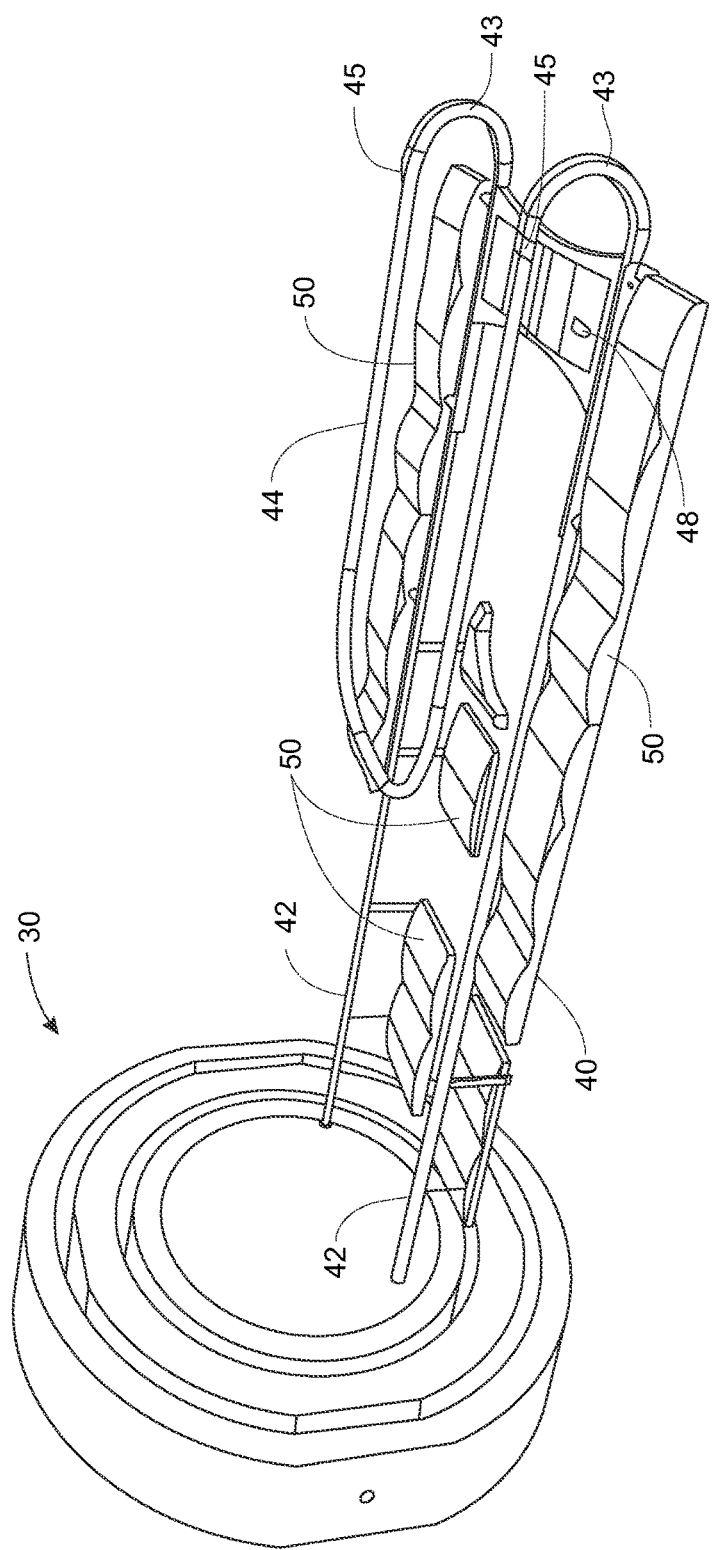
FIG. 4 is a perspective view of the support system without a patient in place.

With further reference to FIGS. 2-5, there is also provided, supported from the legs 42, one or more sections of padding 50. As illustrated in the schematic view of FIG. 2, the padding can include a set of lower padding 50A supported at the respective legs 42 and upper padding 50B supported from the restraining bar 44. As illustrated in FIG. 4, there is also provided a cranial tongue 48 used for head support. Other padding can be appropriately supported from either of the legs 42 to support the other portions of the body including the legs and thighs. The padding 50 can be constructed of a soft material such as a plastic foam material with an appropriate fixed and/or removable cover, such as a commercially available anti-bacterial sheet material or a disposable covering. Another embodiment of support padding is illustrated hereinafter, and described in FIG. 23 in which the padding is inflatable. All of the padding 50 that is illustrated herein is positioned so that the legs and arms of the patient are properly supported. The turned ends 43 accommodate the patient's shoulder area and thus the padding on each side of the legs 42 is disposed slightly outboard of the legs 42 for proper support of the patient's legs, arms and other portions of the body of the patient.

Figure 10A:
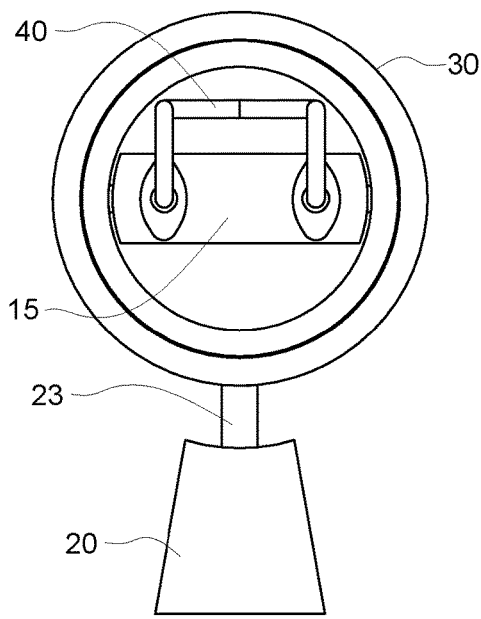
FIGS. 10A and 10B is a schematic view of alternate embodiments for varying system elevation.
Figure 10B:
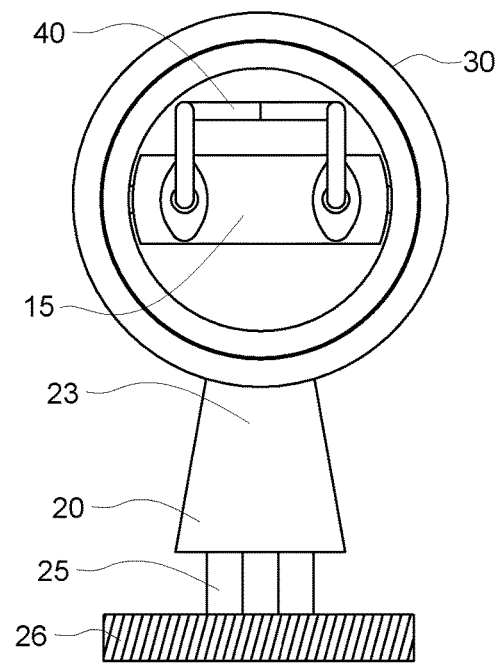
Figure 11:
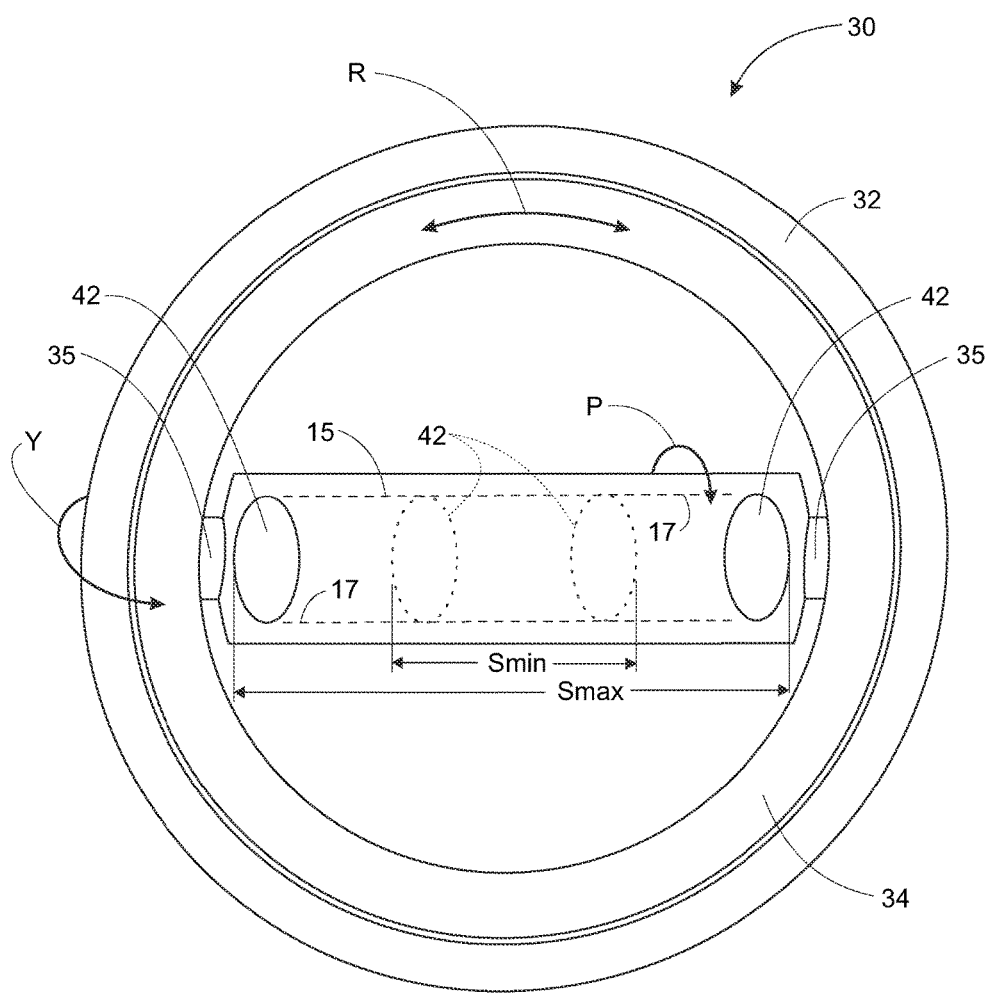
FIG. 11 is a schematic view of the ring structure of the surgery table of the present invention.

Reference is now made to FIGS. 7-11 for further illustrations of the different degrees of freedom or degrees of motion of the table system of the illustrative embodiment. These motions have been discussed previously in connection with FIG. 1. FIGS. 7A, 7B and 7C illustrate differing positions for the "roll" motion, with (FIG. 7A) and without (FIGS. 7B and 7C) a patient supported on the table. This degree of freedom thereby controls the rotation of the patient. This rotation can be through a full 360 degrees of rotation, or can define a lesser degree (e.g. 90 degrees in each rotational direction). Refer now to the diagram in FIG. 11 that shows the ring structure 30. As described above, the ring structure 30 is comprised of an outer ring 32 that is basically non-rotatable and an inner ring 34 that is capable of rotation relative to the outer ring 32. The aforementioned bar member 15 which supports the platform legs 42 is coupled on the inside to the inner ring 34. This coupling, as illustrated in FIG. 11, is by way of a rotation joint 35 that is disposed at respective ends of the bar member 15. The rotation of the inner ring 34 relative to the outer ring 32 is represented in FIG. 11 by the rotation arrow R. FIG. 11 also illustrates by arrow Y the "yaw" direction of motion. FIG. 11 also illustrates by arrow P the "pitch" motion. Thus, in FIGS. 7B and 7C, the bar member 15 and associated platform 40 are shown in two separate "roll" positions in each of opposing rotational directions (from horizontal) based upon the function of the inner ring 34 rotating relative to the outer ring 32.

Figure 8A:
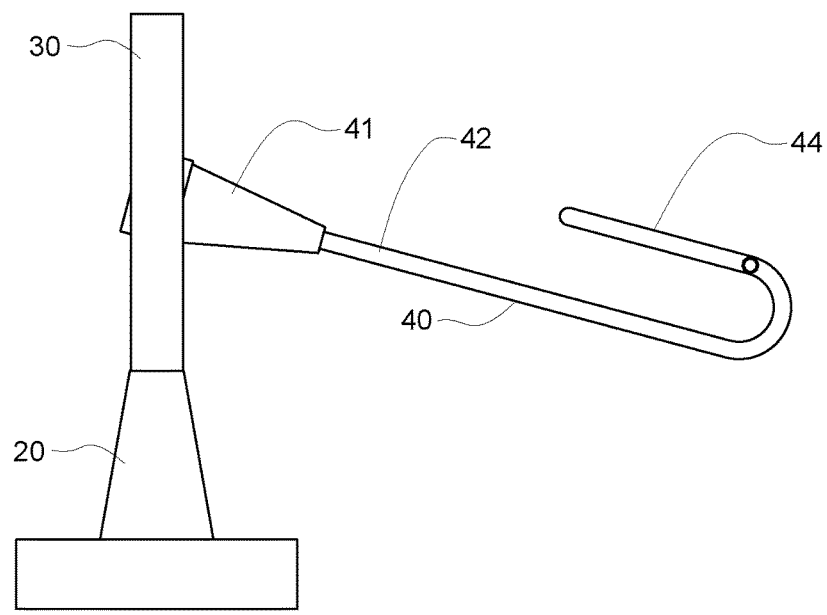
FIGS. 8A and 8B are schematic views illustrating the system's "pitch" parameter.
Figure 8B:
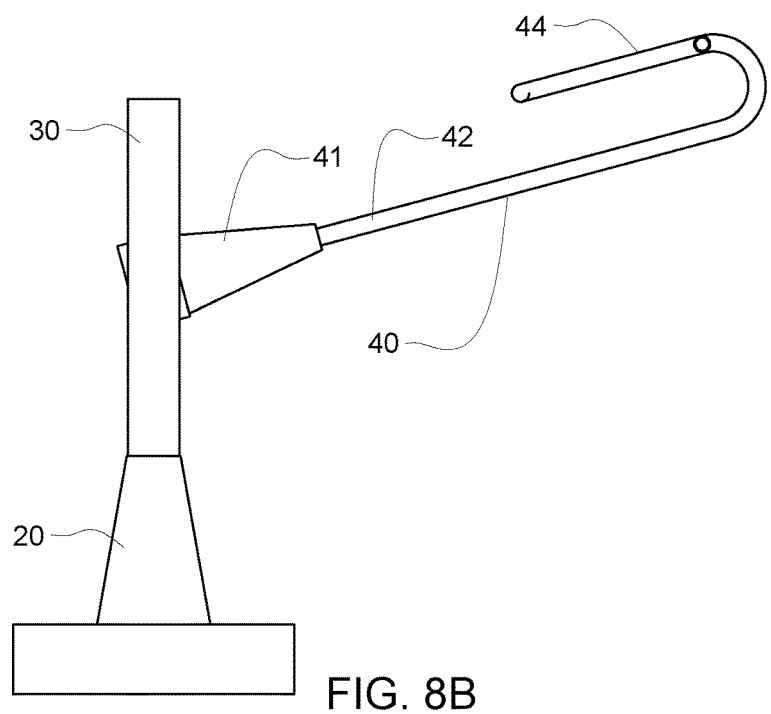

Reference is now made to FIGS. 8A and 8B for an illustration of the "pitch" motion. As indicated previously, the platform is secured at the bar member 15. FIG. 11 illustrates the ends of the legs 42 disposed at the bar member 15. By controlling the rotation joints 35, the bar member 15 can pivot through at least a limited amount of rotation. This is illustrated in FIGS. 8A and 8B by respective downward and upward rotation from the horizontal. The degree of pitch is generally no more than 30 degrees to the horizontal in either direction. The "pitch" can be controlled my motor assembly (e.g. electrical, hydraulic or pneumatic) to rotate the bar member 15 relative to the inner ring 34. The position illustrated in FIG. 8A is often termed the Trendelenburg position with the feet higher than the head by generally 15-30 degrees. FIG. 8A illustrates the reverse Trendelenburg position in which the patient's body is tilted in the opposite direction.

Figure 9A:
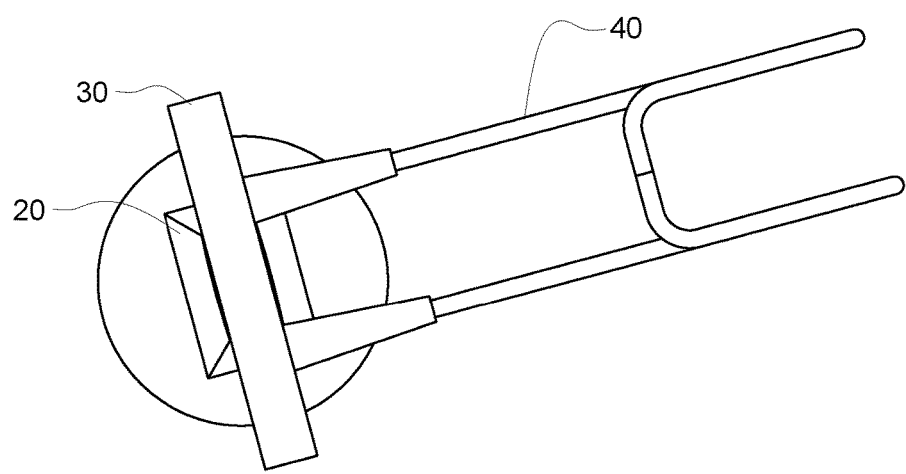
FIGS. 9A and 9B are schematic views illustrating the system's "yaw" parameter.
Figure 9B:
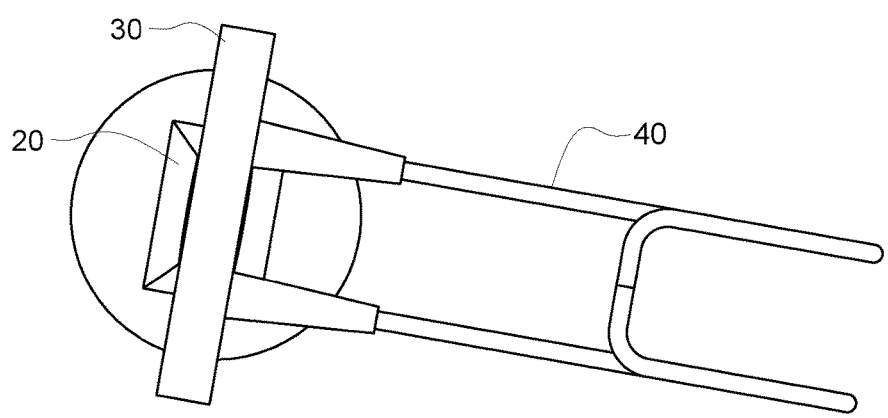
Figure 20A:
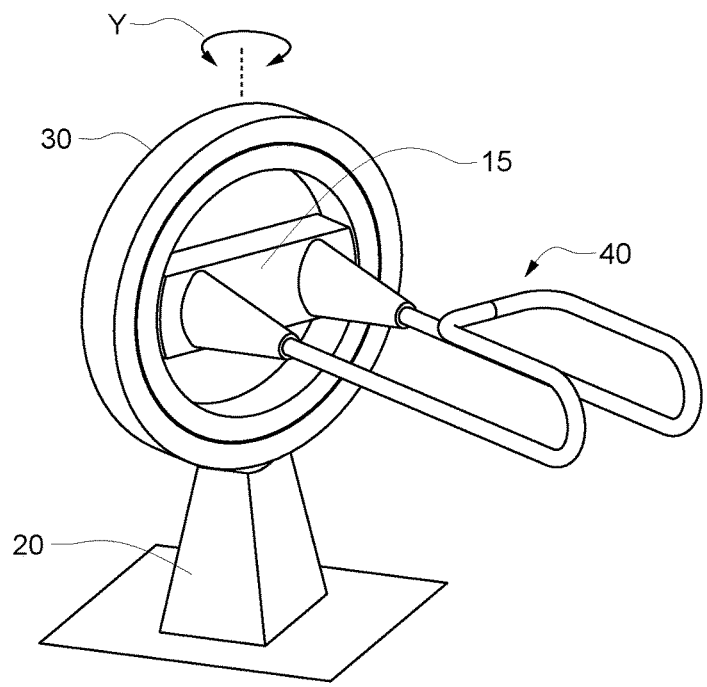
FIGS. 20A and 20B are schematic perspective views illustrating different respective mechanisms for driving and controlling "yaw;"
Figure 20B:
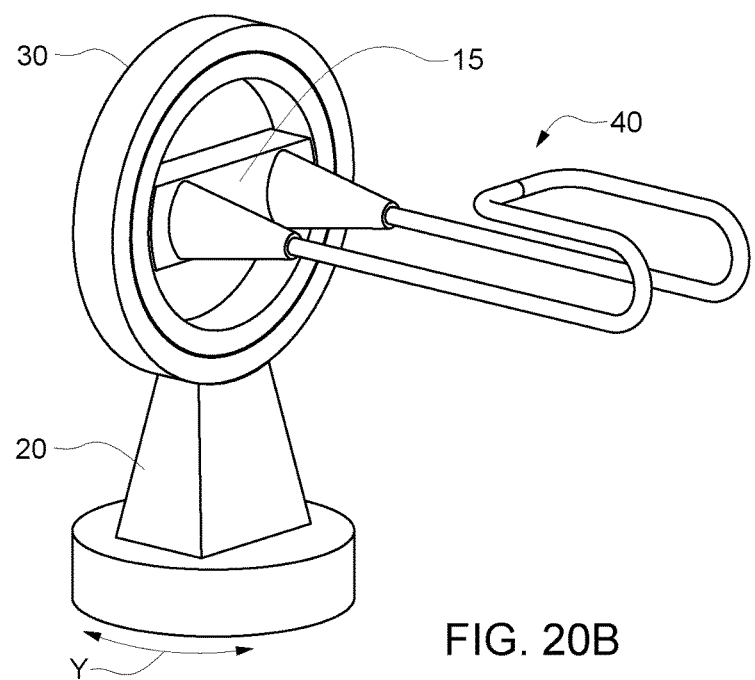

Reference is now made to FIGS. 9A and 9B for an illustration of the "yaw" motion. This rotation is capable of being through at least 270 degrees. This motion controls the position of the patient for, not only surgical procedures, but also for imaging as described above in connection with FIG. 1 herein. This yaw direction motion is performed by either rotation of the entire structure including the pedestal and ring structure, or by rotation of the ring structure only relative to the pedestal. In this regard, refer to the schematic diagrams of FIGS. 20A and 20B. FIG. 20A illustrates the ring structure 30 being rotatable on element 31 relative to the pedestal 20. On the other hand, FIG. 20B illustrates the entire structure including the pedestal 20 and the ring structure 30 together rotatable in the direction of arrow Y so as to provide the aforementioned "yaw" motion. In either case a drive motor of various types can be used to rotate either the entire pedestal and ring structure or the ring structure relative to the pedestal.

Referring again to FIG. 1, one of the other motions depicted is the adjustment of elevation, represented in FIG. 1 by the arrow E. Further potential embodiments are illustrated in FIGS. 10A and 10B regarding the adjustment of elevation. FIG. 10A illustrates a pedestal or base 20 that is connected to the ring structure 30 by a variable elevation element 23. Element 23 can be fixedly attached to the outer ring of the ring structure and can essentially telescope with the pedestal 20 so as to provide a variable distance between the pedestal and the ring structure so as to essentially adjust the elevation of the ring structure and thus in turn the elevation of the patient support platform 40. FIG. 10B on the other hand illustrates a pedestal 20 that can be considered as fixed to the outer ring of the ring structure 30. The variable elevation is provided by elements 25 that enable the entire pedestal and ring structure to be moved to different elevations so as to adjust the elevation position of the patient. In FIG. 10B the elements 25 can be in the form of multiple sleeves used to raise and lower the pedestal 20. There can be a variation in height of up to 12 inches. Screw jacks or hydraulics can be used as part of the elements 25, as well as drive motor assembly. If multiple sleeves are used, these sleeves are positioned for support from and extension from the base 26.

FIG. 11 has been described previously in connection with further details of the ring structure 30 which includes the outer ring 32 and the inner ring 34. Both of these rings can be of substantially cylindrical construction and appropriate drive assembly are described hereinafter in connection with the ring movement. FIG. 11 also illustrates in solid outline the position of the legs 42. This can be considered as a maximum position indicated in FIG. 11 by the dimension $S_{max}$. This dimension can be in the order of approximately 68 cm in an embodiment. Also illustrated in FIG. 11 is a more inward position of the legs 42 illustrated in dotted outline and identified by a minimum spacing of $S_{min}$, which can be approximately 30 cm in an embodiment. Other ranges of maximum and minimum spacing distance are expressly contemplated in alternate embodiments. The varied spacing of the legs is adapted to accommodate differing size patients with a general range of expected physiology in the general population. In an embodiment, the support of particularly sized patients is further facilitated by a guide channel 17 along which the legs 42 can be moved to various spacing distances therebetween. In association with the variation of the spacing of the legs, a section 49 of the restraining bar 44 (FIG. 6) can be provided as an adjustable component. In this manner, the section 49 moves in conjunction with the restraining bar 44 as the spacing is adjusted. The section 49 can be provided as a pair of telescoping, coaxial tubes to allow for such movement in an illustrative embodiment.

Figure 12:
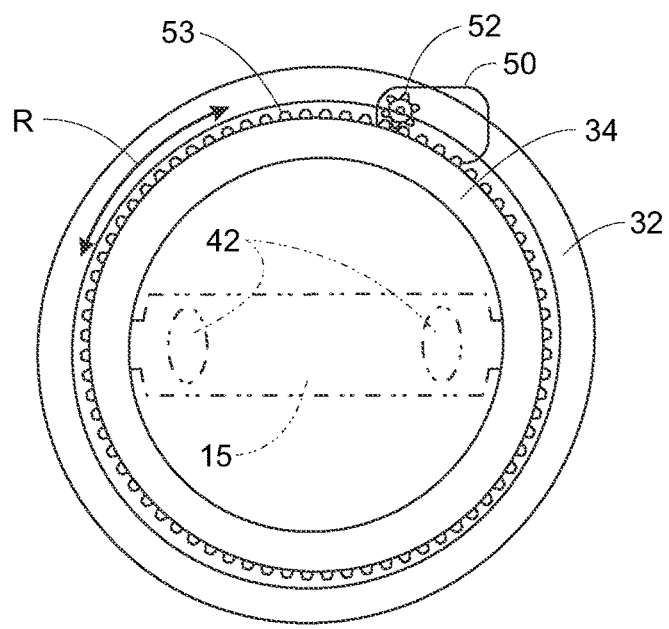
FIG. 12 is a schematic view showing the action of the "roll" actuator.

Reference is made to the schematic diagram of FIG. 12 that illustrates the rings 32 and 34, along with, in dotted outline, the bar member 15 and legs 42. The diagram of FIG. 12 is meant to illustrate the "roll" motion of the embodiment. In this regard, there is provided a motor 50 appropriately mounted at the ring structure. The motor 50 drives a pinion gear 52 which in turn is engaged with the circular rack 53. Selective drive of the motor 50 will rotate the inner ring 34 relative to the outer ring 32 as previously described. The motor 50 can be a servomotor, a stepper motor, or alternatively, the drive can be hydraulic or pneumatic to control the rotation of the inner ring 34.

Figure 13:
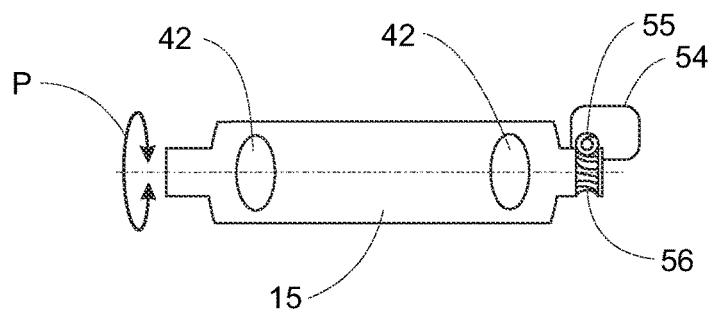
FIG. 13 is a schematic view showing the action of the "pitch" actuator.

Reference is now made to FIG. 13 for an illustration of a "pitch" actuator arrangement. As indicated, in connection with the description of FIG. 11, in order to control the "pitch" the bar member 15 is rotated. This is indicated in FIG. 13 by the rotation arrow P. Thus, the aforementioned rotation joint 35 shown in FIG. 11 is represented in FIG. 13 by the combination of a drive motor 54, a worm gear 55 and a pinion gear 56. Other types of gear or motor arrangements can also be used for controlling the rotation of the bar member 15. The control of the motor can be by, illustratively, a servo type motor or a stepper motor. Also, hydraulic or pneumatic actuators can be used for driving the bar rotation member.

Figure 16:
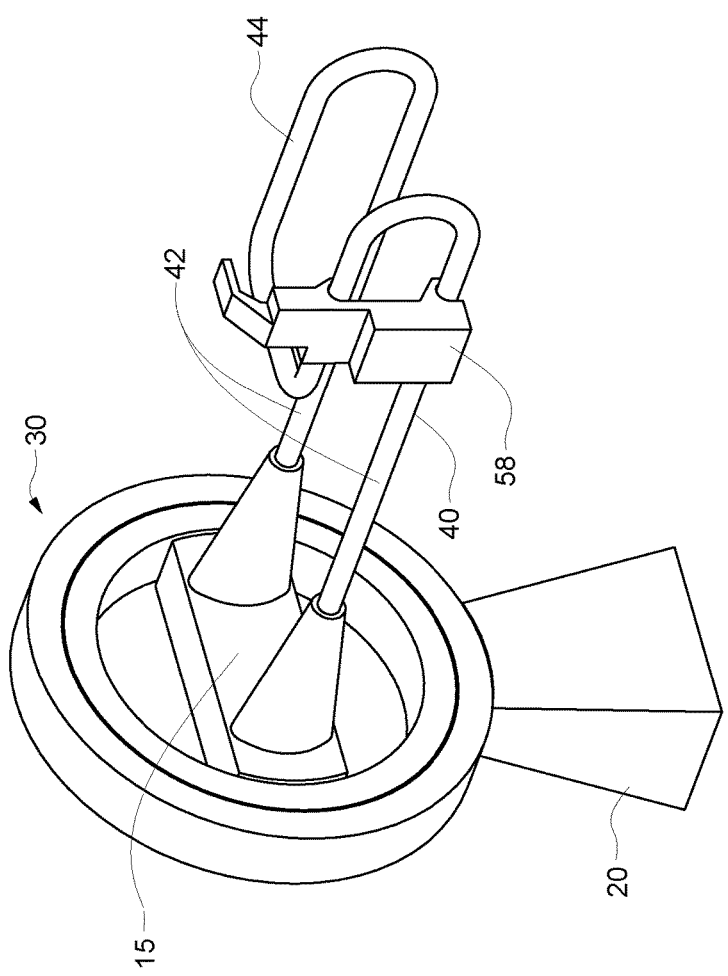
FIG. 16 is a perspective view illustrating an attachment for surgical tools, sensing devices and/or robotic members.
Figure 25:
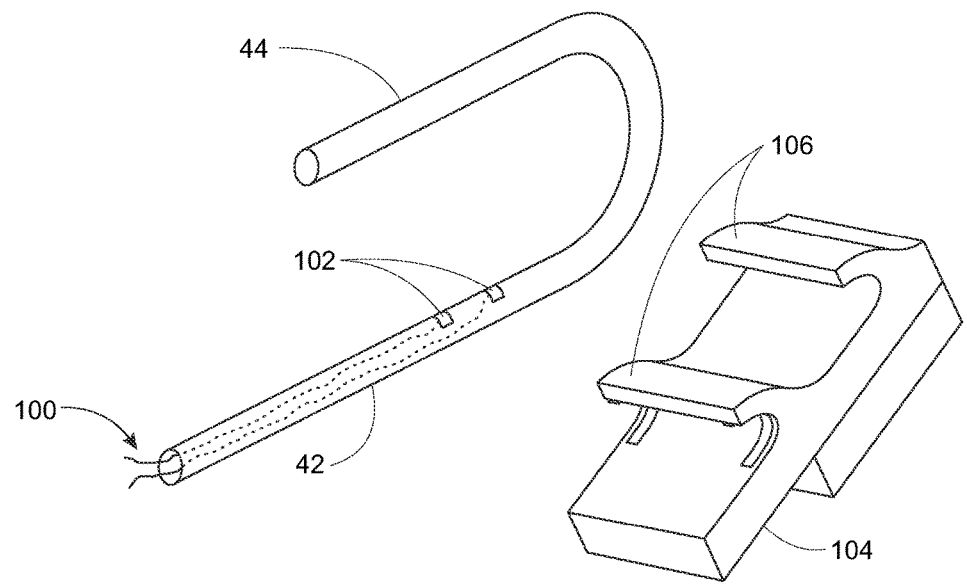
FIG. 25 is an explodes, partially exposed perspective view of an exemplary accessory or tool adapted to be mounted on the surgical table rails according to an embodiment the platform.

FIG. 16 illustrates the basic surgery table including the pedestal 20, ring structure 30 and platform 40. The additional system shown in FIG. 16 includes a tool mounting device 58 that is supported between one of the legs 42 and the restraining bar 44. Another accessory tool is illustrated in FIG. 25 and discussed in further detail hereinafter. The tool mounting device 58 can be used for mounting other tools including manually operable tools as well as robotic tools.

Figure 17:
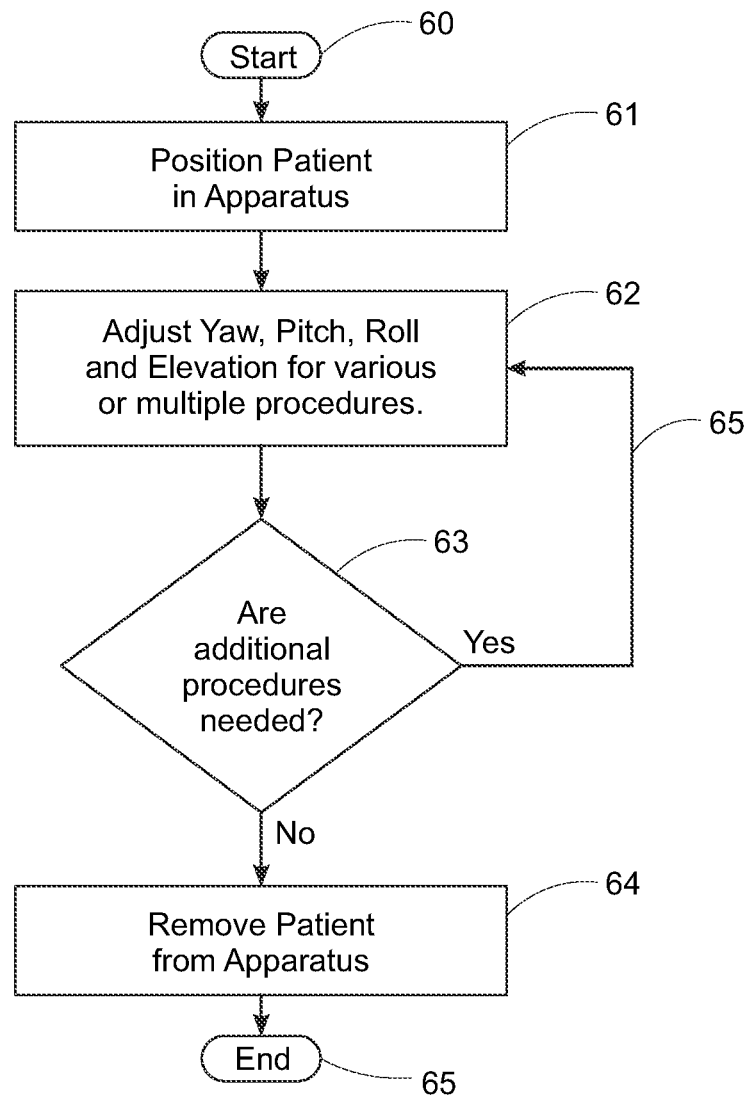
FIGS. 17 and 18 are block diagrams of associated procedures for the operation of the system and method.

FIG. 17 is a block flow diagram illustrating a series of surgical or medical procedures performed with the system of the illustrative embodiment. From a start position 60, the patient is positioned on the system as indicated by box 61. Next, there are adjustments of any one or more of "yaw," "pitch" and "roll" as well as possibly elevation for various or multiple procedures. This is illustrated in FIG. 17 by the box 62. The next step includes a decision box 63 to determine whether additional procedures are needed. If additional procedures are needed, then feedback by way of line 66 returns to box 62. If additional procedures are not needed, then the patient is removed from the system as indicated by box 64 to the end 65.

Figure 18:
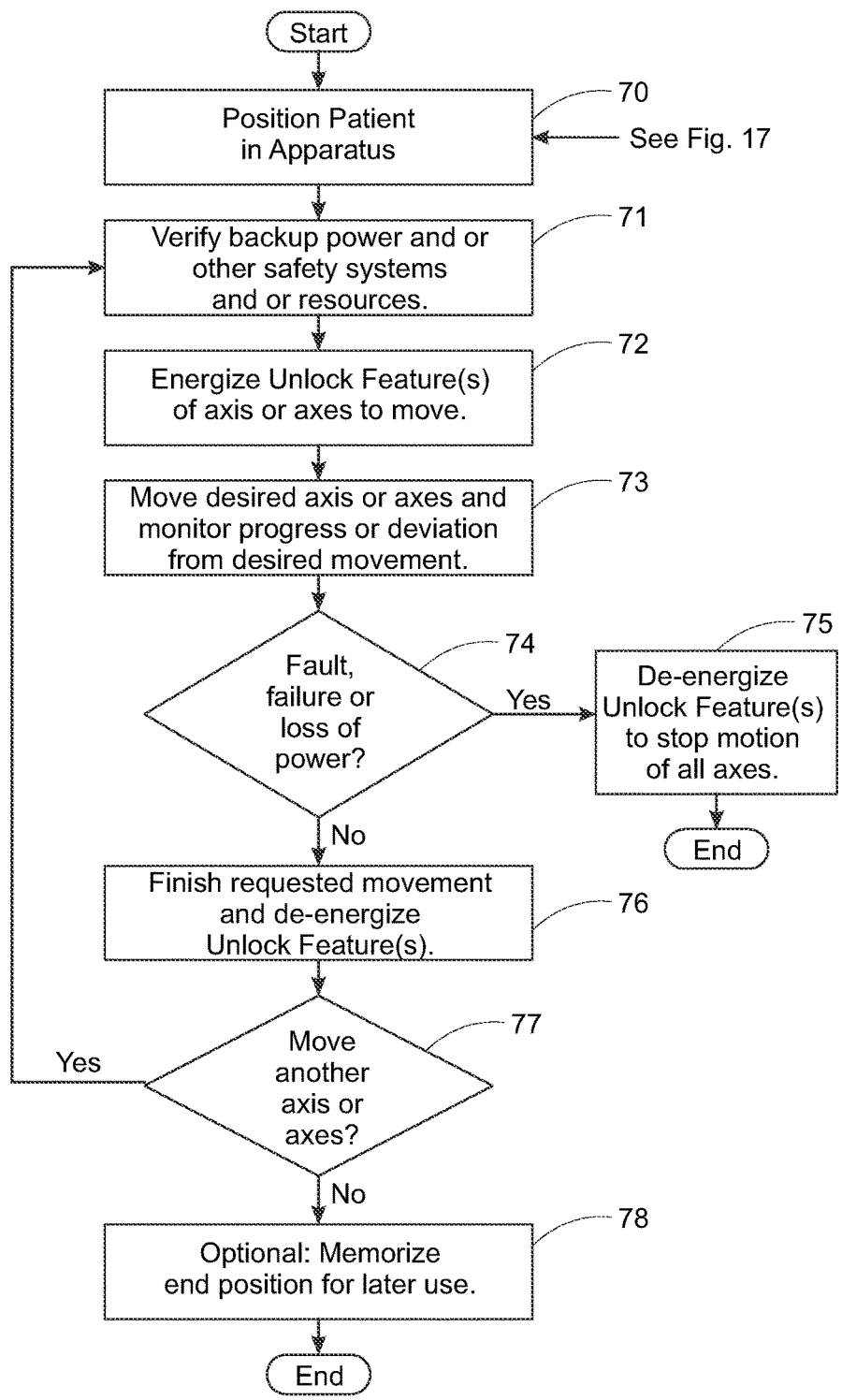

FIG. 18 is a further, more detailed, block flow diagram that also incorporates certain locking features to be described in more detail hereinafter. At the start box 70 indicates the positioning of the patient in the system. Following that, box 71 verifies certain parameters such as the operation of sensors and actuators. Following that, box 72 indicates that the unlock feature is energized so as to allow the motions. Following that, box 73 indicates that certain of the described motions are performed along with monitoring the progress and monitoring any deviation from the desired movement. The decision box 74 asks whether there has been a failure or loss of power. If there has been a loss of power, then box 75 indicates that the unlock feature is de-energized or essentially a locking occurs to stop motion of all axis. If a fault or failure of power does not occur, then the requested movement is finished and the unlock feature is de-energized. The decision box 77 then asks the question as to whether or not to move to another axis. A "yes" decision repeats the cycle back to box 71. A "no" decision leads to box 78 which can memorize an end position for a later use.

Figure 19:
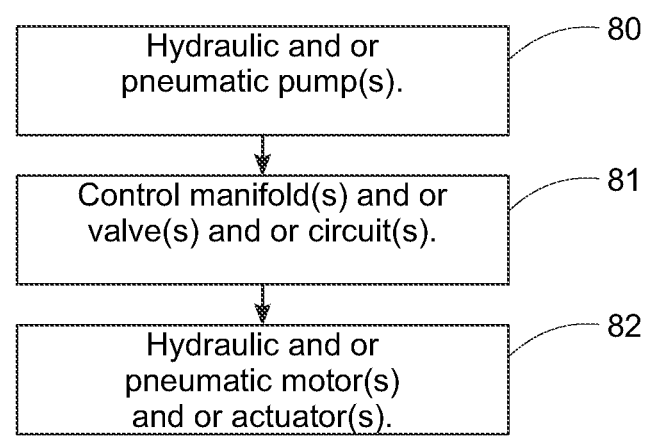
FIG. 19 is a block diagram schematically illustrating alternate forms of control including fluid-based control and power systems, such as hydraulics and/or pneumatics.

FIG. 19 is a further simple block diagram that illustrates the universal nature of the control of the system of the illustrative embodiment. As mentioned previously, drive motors can be controlled by electrical signals from an electrical controller. However, alternatively, hydraulic and/or pneumatic pumps can be used as indicated by box 80 in FIG. 19. These pumps can in turn control such items as manifolds, valves or circuits as indicated by box 81. Lastly, box 82 indicates control of hydraulic and/or pneumatic motors and/or actuators.

Figure 21A:
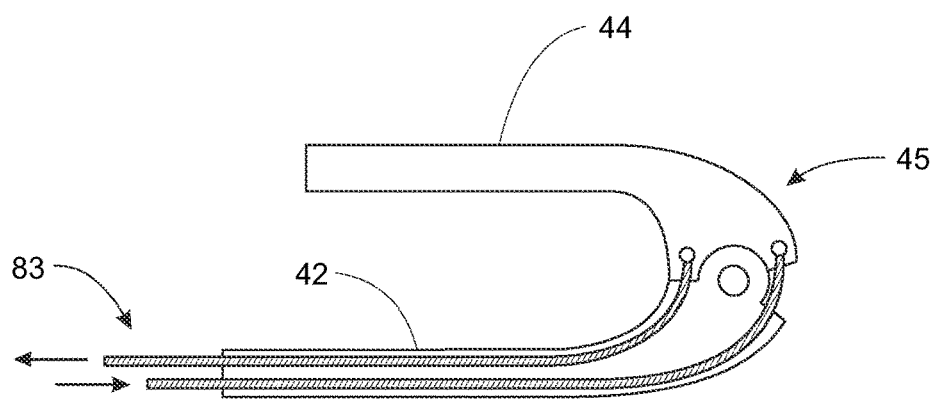
FIGS. 21A and 21B are exposed side views respectively illustrating closed and open positions for cable-based, surgical table restraining bar mechanism and associated cable actuation.
Figure 21B:
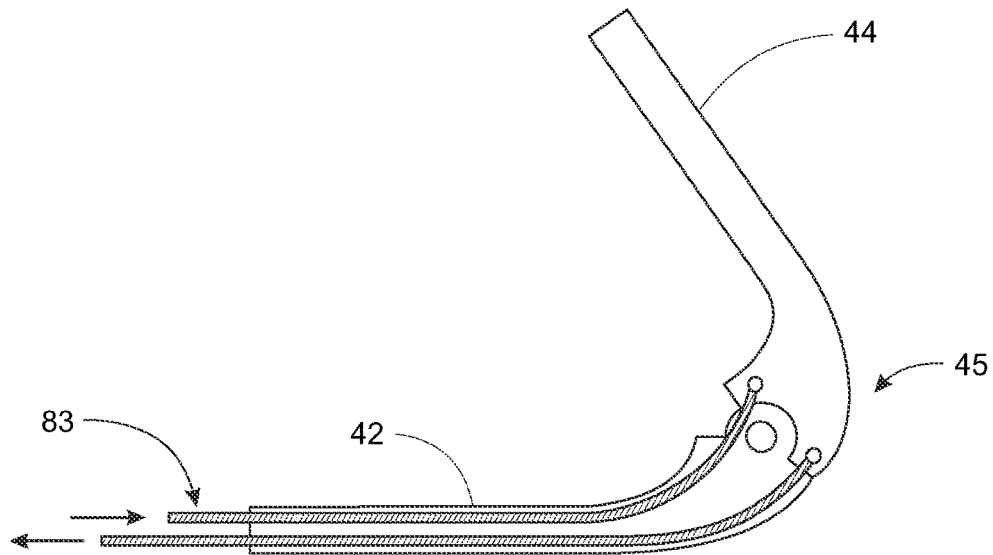

In FIG. 14 the restraining member 44 is indicated as movable at a pivot 45. The restraining member 44 can be controlled manually, although, in an embodiment, a form of cable actuation can be used, as illustrated in FIGS. 21A and 21B. In this embodiment in FIG. 21A, the restraining member 44 is shown in its closed position and in FIG. 21B the restraining member 44 is shown in an open position. These positions are controlled by illustrative cabling 83 that connect to and terminate at the restraining member 44. The cabling 83 can couple through each of the respective legs 42. The direction of arrows, in FIGS. 21A and 21B, illustrates the pushing or pulling of cables in order to perform the desired pivoting at the hinge location 45.

In the operation of the system of the illustrative embodiment once a particular position is attained by the motion control, it is desirable that the selected position is locked in place. Moreover, locking is employed to hold the patient in place. Various embodiments are described herein for these various locking features.

Figure 22A:
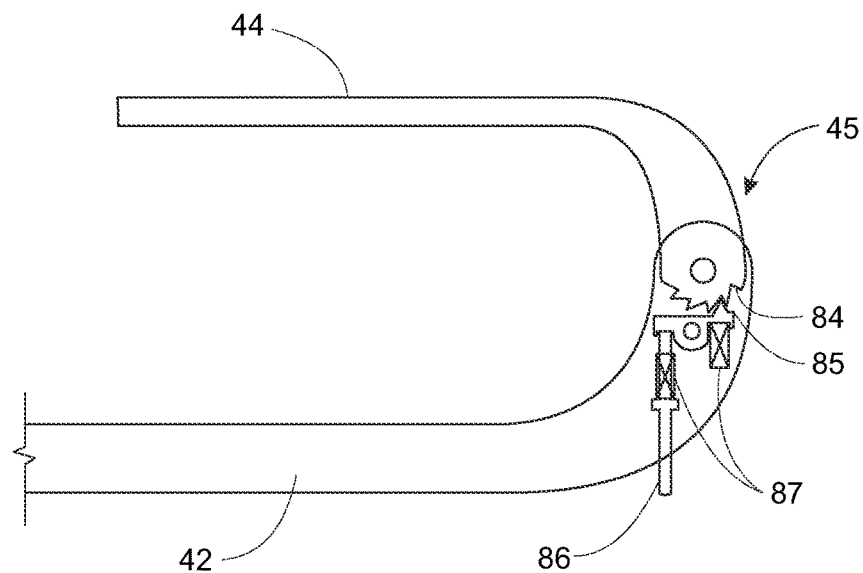
FIGS. 22A and 22B are exposed side views respectively illustrating different locking mechanisms for the restraining bar mechanism.
Figure 22B:
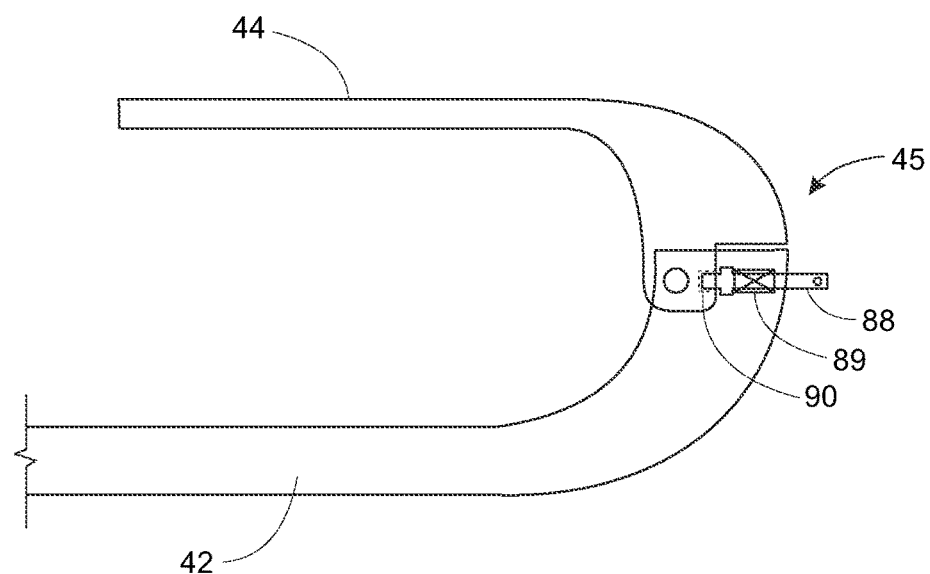

FIGS. 22A and 22B illustrate slightly different embodiments of a locking mechanism that is used for locking the relative position between the restraining member 44 and the legs 42. In the schematic diagram of FIG. 22A, there is illustrated a pivot at the hinge location 45, including ratchet teeth 84 that can engage with a pawl 85. A release button 86 can pivot the pawl 85 so as to disengage the pivot and allow a pivoting of the restraining member 44 to enable release of the patient. Appropriate springs 87 (e.g. compression springs) can be provided on both the release button 86 and the pawl 85. FIG. 22B illustrates another form of locking mechanism including a retractable lock pin 88, a spring 89 and a catch mechanism 90. The lock pin 88 is shown in its normal locked position but can be manually retracted in order to enable a pivoting between the legs 42 and the restraining member 44.

Figure 23A:
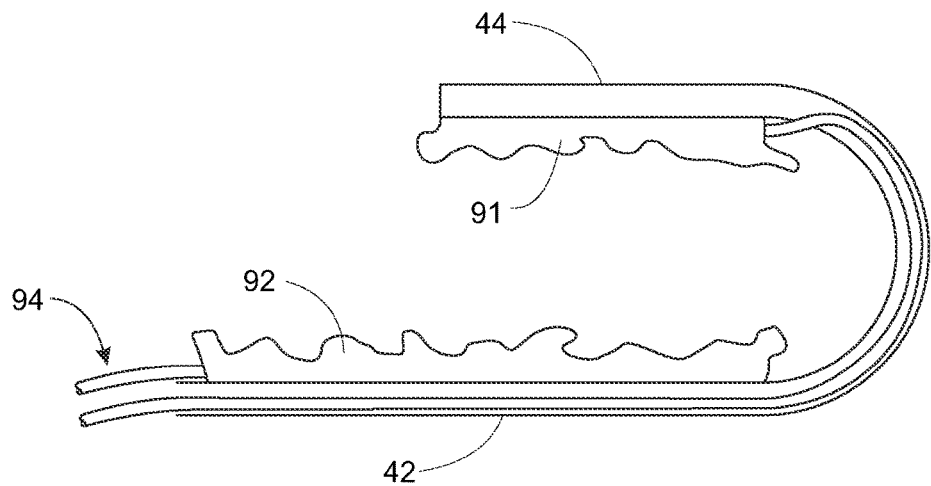
FIGS. 23A and 23B are schematic side views respectively illustrating patient engagement pads in deflated and inflated positions so as to selectively conform to the particular size of the patient and ensure a positive grip thereof.
Figure 23B:
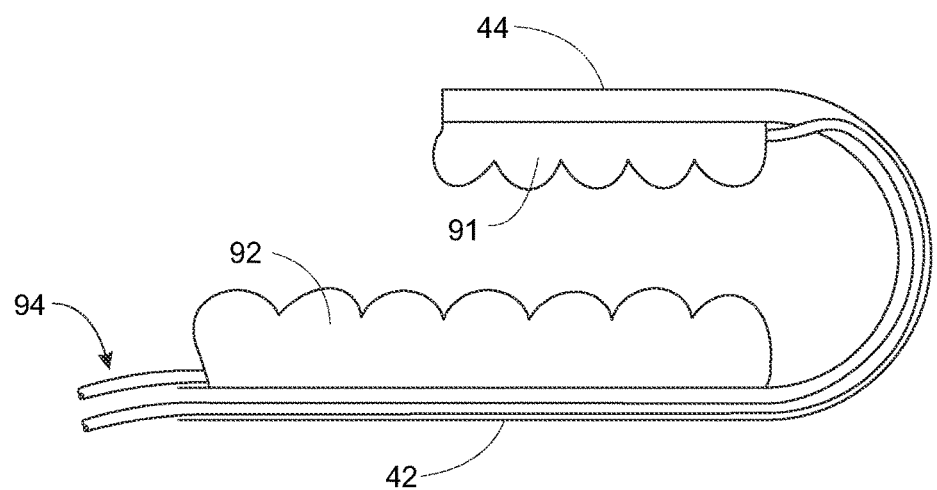

Reference is now made to FIGS. 23A and 23B for an illustration of a further aspect of the illustrative embodiment in which the rest pads can be inflatable pads. For simplicity, in FIGS. 23A and 23B all that is illustrated is a portion of the leg 42 and the restraining member 44. In FIG. 23A the pads 91 and 92 associated respectively with the member 44 and leg 42 are shown in a deflated or collapsed position. On the other hand, in FIG. 23B the pads 91 and 92 are shown in their inflated position pressing against an arm or other portion of the body of the patient. FIGS. 23A and 23B only illustrate pads adjacent to the shoulder area of the system. However, it is understood that inflatable pads can be used at other locations in contact with other portions of the patient's body. FIGS. 23A and 23B also illustrate pneumatic tubes 94 that extend respectively to the pads 91 and 92. A hydraulic arrangement can also be used to inflate the different pads.

Figure 24:
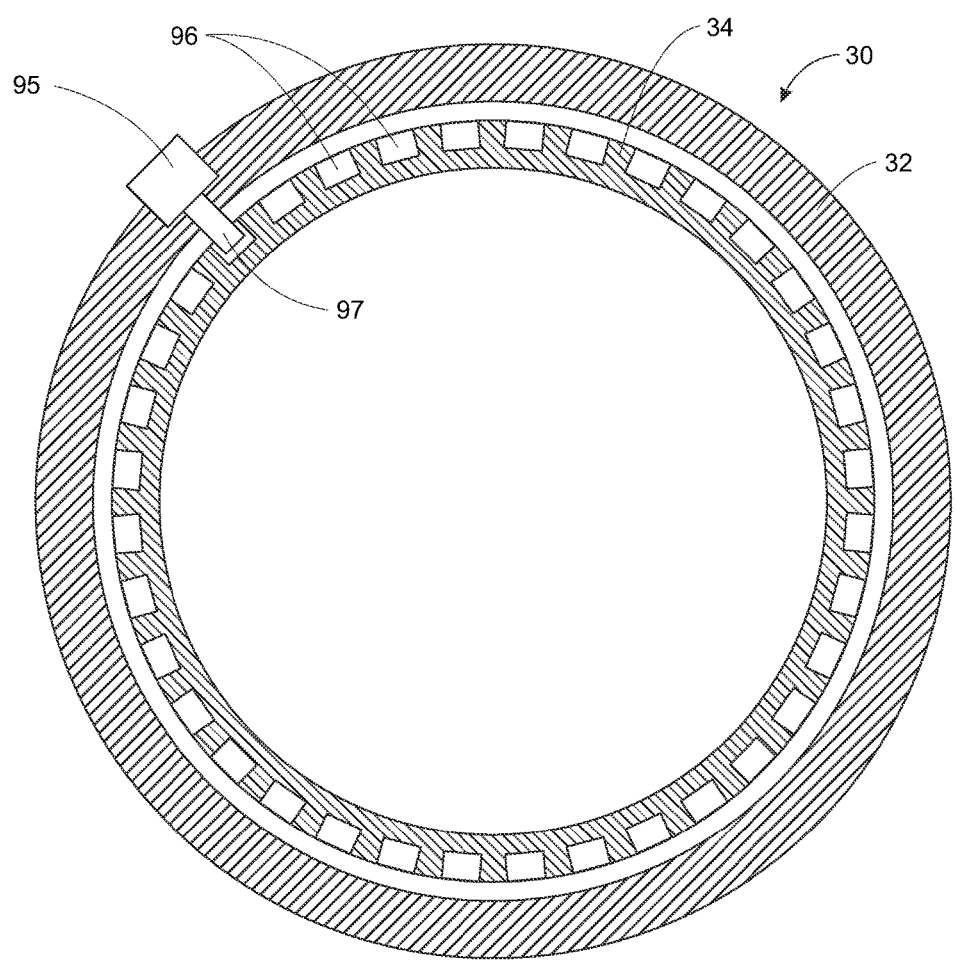
FIG. 24 is a cross section schematically illustrating an embodiment of the ring structure employing a locking pin and actuator assembly.

In FIGS. 22 and 23, various locking mechanisms are described in association with the locking of the restraining member 44 relative to the legs 42. FIG. 24 illustrates a further locking mechanism that can be associated with the ring structure 30. FIG. 24 shows the outer ring 32 of the ring structure 30 supporting an actuator 95. The actuator 95 can be controlled electronically, pneumatically or hydraulically. The inner ring 34 is provided with a series of detents or notches 96 that are adapted to be engaged by the locking pin 97 of the actuator 95. The pin 97 allows an indexing of the relative members in this embodiment as well as in other embodiments described herein. As indicated previously, it is the inner ring 34 that is driven relative to the outer ring 32, such as illustrated in FIG. 12. The locking action is coordinated with the rotation so that the locking occurs at the proper time. The locking feature assures that the support table will be maintained in the proper "roll" position.

Figure 26:
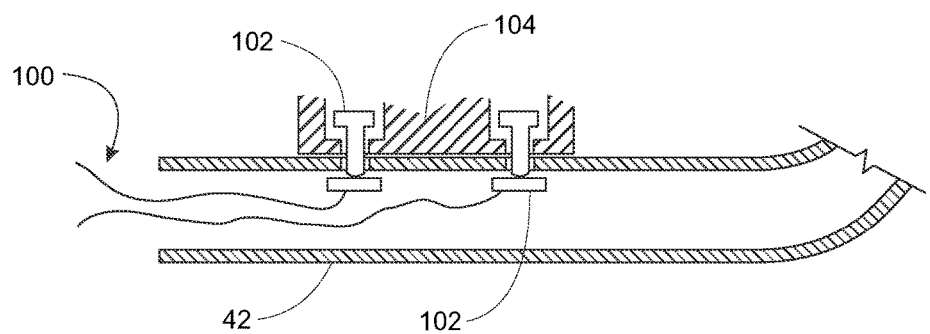
FIG. 26 is a partial cross section of the accessory or tool base operatively engaged in the rail of FIG. 25.

Reference is now made to FIGS. 25 and 26 for further schematic illustrations of the platform structure. At least the platform can be constructed of tubular type enabling wiring 100 to extend through the legs to electrical contacts 102. FIGS. 25 and 26 also illustrate an accessory tool 104 having spaced apart arms 106 that are meant to engage with the platform. Refer also to the schematic perspective view of FIG. 16 showing a tool mounting device 58. The accessory tool 104 can be mounted in a similar manner between the retaining member and legs. This arrangement thus enables the coupling of electrical wiring which can be coupled directly from the pedestal through the leg tubing to the accessory tool 104. This can provide electrical communication to other tools that can be mounted from the accessory tool 104 or the previously described tool mounting device 58 in FIG. 16.

Figure 27:
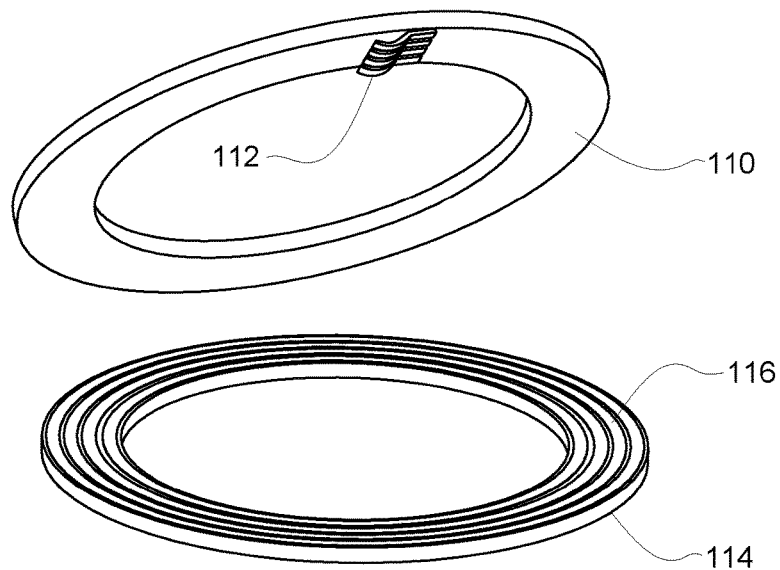
FIGS. 27 and 28 are each exploded schematic perspective views showing a plurality of contact rings and pads that enable cableless interconnection of the surgical table to the base and external components.
Figure 28:
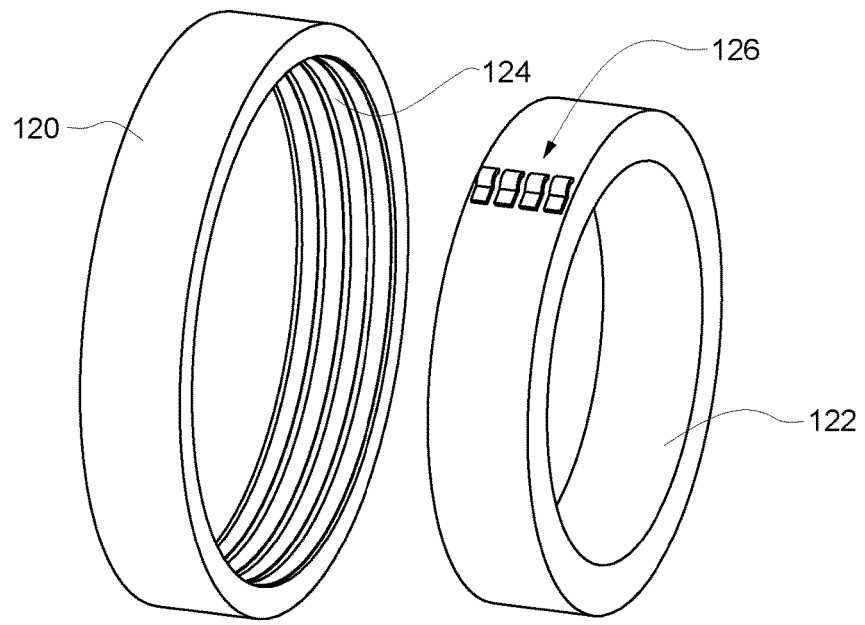

Reference is now made to FIGS. 27 and 28 for schematic representations of other ways that electrical contacts can be incorporated into the table structure. In FIG. 27 the member 110 carries individual-spaced electrical contacts 112 and the associated member 114 carries circular contacts 116. These members 110 and 114 can represent rings of the ring structure and are shown simply in schematic form in FIG. 27. Any rotation between the members 110 and 114 will maintain electrical contact between the contacts 112 and 116. This arrangement can be used to maintain electrical communication from a base member of the system to more remote tools to assist in or control operation of such tools. Reference is now also made to FIG. 28 which shows cylindrical members 120 and 122 with respective electrical contacts 124 and 126.

Figure 29:
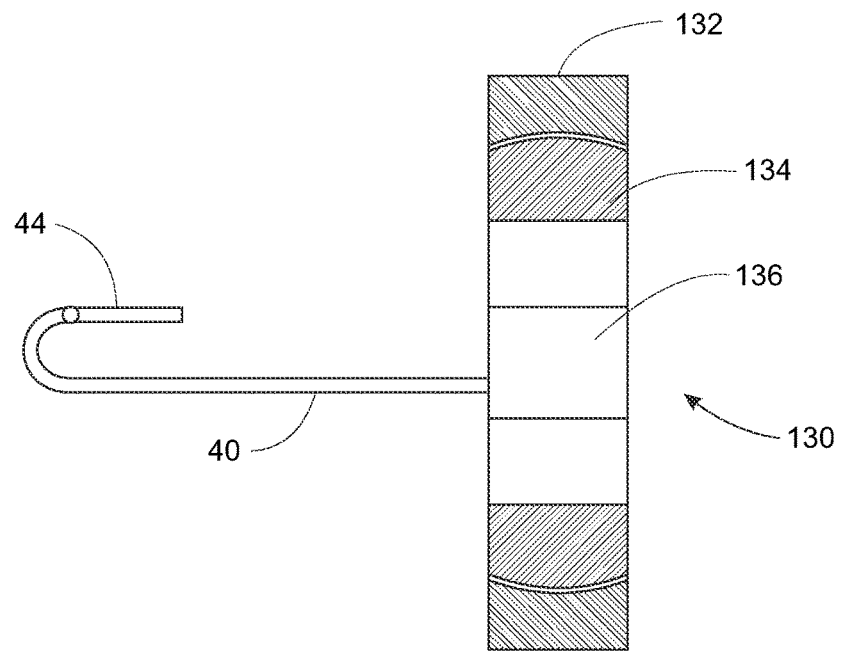
FIGS. 29 and 30 are schematic side cross sections of an alternate embodiment of ring structure employing a ball and socket arrangement to provide at least three degrees of freedom using one fixed socket and a movable ball elements.
Figure 30:
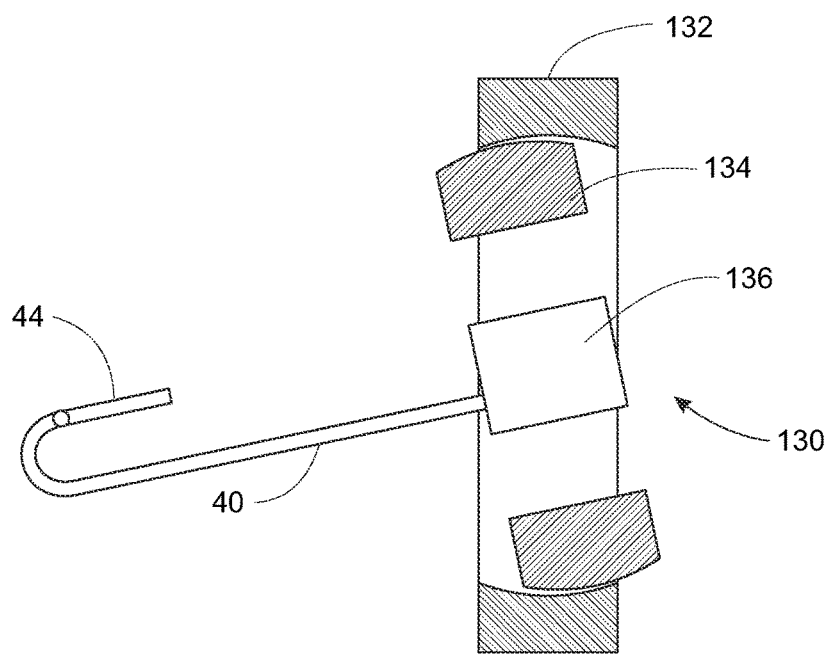

Reference is now made to an alternate embodiment of the embodiment illustrated in FIGS. 29 and 30 in which the ring structure 130 comprises inner and outer rings that are not cylindrical as previously described in, for example, in FIG. 6, but instead are comprised of a partial spherical socket arrangement including an outer member 132 and an inner member 134. As in the previous embodiment, the bar member 136 is supported across the ring member 134 but in this embodiment does not pivot relative to the ring member 134. Instead, the ring member 134 is capable of a rotation such as to a position illustrated in FIG. 30. This rotation or tilting of the inner ring member 134 relative to the outer ring member 132 controls the "pitch" motion. As the "pitch" motion is controlled by the ball and socket arrangement between the rings 132 and 134, the bar member 136 can be fixed in position at the inner ring. In this embodiment the ball and socket arrangement enables control of both "pitch" and "roll" of the table. This control can be by motorized/automated control of the ball and socket separately. The "roll" rotation can be accomplished using a mechanism such as that as shown in FIG. 12, while the "pitch" motion can be controlled by orthogonal motion control between the inner and outer rings.

It should be clear that the above-described surgical table, in various forms enables the surgeon or other practitioner to achieve significantly enhanced efficiency, flexibility and convenience in the performance of a surgical procedure in which one or more imaging modalities are employed. This system and method ensures greater accuracy and shorter time for the patient in the operative environment, as the need to relocate the patient between different surgical and imaging venues is eliminated. Likewise, the available range of imaging modalities can be increased.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, while the system and method of the illustrative embodiment is shown in connection with multiple imaging devices, it is contemplated that a single imaging device can be provided in alternate embodiments or that the surgical table of the system and method can be employed in an environment free of any slidable imaging devices. Likewise, while the slidable imaging devices are shown movably supported on overhead rails, a floor track or other guiding mechanism that facilitates passage of the device over the patient on the stationary table are expressly contemplated. Furthermore, the types of imaging devices employed are variable from those depicted and described. Non-ring-like imaging devices, and other types of slidable devices can also be employed, and further devices can be located at another "yaw" position, such as the 90-degree and 270-degree position. Accordingly, this description is meant to be taken only by way of example, and not to otherwise limit the scope of this invention.

What is claimed is:

1. A system for supporting a patient during a medical procedure, comprising:
   a pedestal supported from a base surface;
   a ring structure mounted over the pedestal, the ring structure including an inner ring and an outer ring that are constructed and arranged for relative rotation therebetween;
   an elongated support platform upon which the patient is supported;
   a bar member connected to and mounted at one end of the support platform and within a circumference of the inner ring of the ring structure while an opposite end of the support platform is free so as to be disposed in a cantilever manner from the ring structure; and
   respective control elements configured to control a roll motion of the support platform by rotating the inner ring relative to the outer ring, a pitch motion of the support platform by pivoting the bar member relative to the inner ring, and a yaw motion of the support platform by rotating the ring structure relative to the pedestal.

2. The system of claim 1 including means for controlling the elevation of the ring structure.

3. The system of claim 2 including means for elevating the ring structure relative to the pedestal.

4. The system of claim 2 including means for elevating the pedestal and ring structure together.

5. The system of claim 1 including inflatable padding on the platform upon which a body part rests or that hold against the body part for restraint thereof.

6. The system of claim 1 wherein the roll motion is controllable through 360 degrees.

7. The system of claim 1 wherein the pitch motion is controlled through an angle on the order of 15-30 degrees both above and below horizontal.

8. The system of claim 1 wherein the yaw motion is controlled through 270 degrees.

9. The system of claim 1 wherein the control elements are controlled by at least one of an electrical, electronic, hydraulic and pneumatic assembly.

10. A system for supporting a patient during a medical procedure, comprising:
    a pedestal supported from a base surface;
    a ring structure mounted over the pedestal, the ring structure including an inner ring and an outer ring that are constructed and arranged for relative rotation therebetween;
    an elongated support platform upon which the patient is supported;
    a bar member for mounting one end of the support platform to the inner ring of the ring structure while an opposite end of the support platform is free so as to be disposed in a cantilever manner from the ring structure; and
    respective control elements configured to control a roll motion of the support platform about a longitudinal axis of the support platform by rotating the inner ring relative to the outer ring, a pitch motion of the support platform by pivoting the bar member relative to the inner ring, and a yaw motion of the support platform by rotating the ring structure relative to the pedestal.

11. The system of claim 1 including means for controlling the elevation of the ring structure.

12. The system of claim 2 including means for elevating the ring structure relative to the pedestal.

13. The system of claim 2 including means for elevating the pedestal and ring structure together.

14. The system of claim 1 including inflatable padding on the platform upon which a body part rests or that hold against the body part for restraint thereof.

15. The system of claim 1 wherein the roll motion is controllable through 360 degrees.

16. The system of claim 1 wherein the pitch motion is controlled through an angle on the order of 15-30 degrees both above and below horizontal.

17. The system of claim 1 wherein the yaw motion is controlled through 270 degrees.

18. The system of claim 1 wherein the control elements are controlled by at least one of an electrical, electronic, hydraulic and pneumatic assembly.

19. A system for supporting a patient during a medical procedure, comprising:
    a pedestal supported from a base surface;
    a ring structure mounted over the pedestal, the ring structure including an inner ring and an outer ring that are constructed and arranged for relative rotation therebetween;
    an elongated support platform upon which the patient is supported, the support platform defining a longitudinal axis, wherein the inner ring and outer ring are concentric about the longitudinal axis;
    a bar member for mounting one end of the support platform to the inner ring of the ring structure while an opposite end of the support platform is free so as to be disposed in a cantilever manner from the ring structure; and respective control elements configured to control a roll motion of the support platform by rotating the inner ring relative to the outer ring, a pitch motion of the support platform by pivoting the bar member relative to the inner ring, and a yaw motion of the support platform by rotating the ring structure relative to the pedestal.

20. The system of claim 1 including means for controlling the elevation of the ring structure.

21. The system of claim 2 including means for elevating the ring structure relative to the pedestal.

22. The system of claim 2 including means for elevating the pedestal and ring structure together.

23. The system of claim 1 wherein the roll motion is controllable through 360 degrees.

24. The system of claim 1 wherein the pitch motion is controlled through an angle on the order of 15-30 degrees both above and below horizontal.

25. The system of claim 1 wherein the yaw motion is controlled through 270 degrees.

26. The system of claim 1 wherein the control elements are controlled by at least one of an electrical, electronic, hydraulic and pneumatic assembly.

* * * * *